US012562279B2

(12) United States Patent
He et al.

(10) Patent No.: US 12,562,279 B2
(45) Date of Patent: Feb. 24, 2026

(54) PORTABLE EDGE AI-ASSISTED DIAGNOSIS AND QUALITY CONTROL SYSTEM FOR GASTROINTESTINAL ENDOSCOPY

(71) Applicant: Hong Kong Applied Science and Technology Research Institute Company Limited, Hong Kong (CN)

(72) Inventors: XueJian He, Hong Kong (CN); Lu Wang, Hong Kong (CN); Ping Shun Leung, Hong Kong (CN); Shangping Liu, Hong Kong (CN); Chi Hin Samuel Chow, Hong Kong (CN); XinDong Liu, Hong Kong (CN); Manu Bangalore Nagaraj, Hong Kong (CN)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 267 days.

(21) Appl. No.: 18/591,111

(22) Filed: Feb. 29, 2024

(65) Prior Publication Data

US 2025/0279199 A1     Sep. 4, 2025

(51) Int. Cl.
　　*G16H 50/20* 　　　(2018.01)
　　*A61B 1/00* 　　　(2006.01)
　　　　　(Continued)

(52) U.S. Cl.
　　CPC ....... *G16H 50/20* (2018.01); *A61B 1/000096* (2022.02); *G06T 7/0012* (2013.01);
　　　　　(Continued)

(58) Field of Classification Search
　　CPC ........ G16H 50/20; G16H 70/20; G16H 30/40; G16H 50/70; A61B 1/000096;
　　　　　(Continued)

(56) References Cited

U.S. PATENT DOCUMENTS 9,934,364 B1 *　4/2018　Kumar .................. G16H 15/00
10,896,352 B2　1/2021　Hsieh et al.
　　　　　(Continued)

FOREIGN PATENT DOCUMENTS

CN　　115004316 A　9/2022
CN　　115984111 A　4/2023
WO　2020215593 A1　10/2020

OTHER PUBLICATIONS

R.-A. Vulpoi et al., "Artificial Intelligence in Digestive Endoscopy—Where Are We and Where Are We Going?" Diagnostics 2022, 12, 927.

(Continued)

*Primary Examiner* — Wesley J Tucker
(74) *Attorney, Agent, or Firm* — S&F/WEHRW

(57) ABSTRACT

In a decision-support system for gastrointestinal (GI) endoscopy, convolutional neural networks (CNNs) are set up to perform decision-support tasks according to endoscopic images. Each learnable kernel used in the CNNs is advantageously modeled as a linear combination of a set of fixed kernels for simplifying kernel learning, giving a lightweight kernel model to advantageously reduce required computation resources. Further computation-resource reduction can be made by CNN model compression via knowledge distillation and by using multi-task CNNs. It enables the decision-support system to be realized as an edge computing system near a site of performing endoscopic examinations. The system can be automatically configured for esophagogastroduodenoscopy (EGD) or colonoscopy. In the system, lesion-detection results and quality-control results can be seamlessly integrated to provide value-added results, which are more valuable to the endoscopist than separately considering the lesion-detection results and quality-control results.

20 Claims, 20 Drawing Sheets

(51) Int. Cl.

| | |
|---|---|
| *G06T 7/00* | (2017.01) |
| *G06V 10/25* | (2022.01) |
| *G06V 10/764* | (2022.01) |
| *G16H 70/20* | (2018.01) |

(52) U.S. Cl.

CPC ............ *G06V 10/25* (2022.01); *G06V 10/764* (2022.01); *G16H 70/20* (2018.01); *G06T 2207/10016* (2013.01); *G06T 2207/10068* (2013.01); *G06T 2207/20081* (2013.01); *G06T 2207/20084* (2013.01); *G06T 2207/30032* (2013.01); *G06T 2207/30096* (2013.01); *G06V 2201/031* (2022.01)

(58) Field of Classification Search

CPC ... A61B 1/000094; A61B 1/31; G06T 7/0012; G06T 2207/10016; G06T 2207/10068; G06T 2207/20081; G06T 2207/20084; G06T 2207/30032; G06T 2207/30096; G06T 2207/30028; G06V 10/25; G06V 10/764; G06V 2201/031; G06V 10/82

See application file for complete search history.

(56) References Cited

U.S. PATENT DOCUMENTS

| | | | | |
|---|---|---|---|---|
| 11,464,491 | B2 * | 10/2022 | Jacob ........................ | G06T 7/60 |
| 11,633,084 | B2 | 4/2023 | Hirasawa et al. | |
| 11,715,201 | B2 * | 8/2023 | Oh ......................... | G16H 30/20 |
| | | | | 600/408 |
| 12,014,488 | B2 * | 6/2024 | Madabhushi .......... | G16H 30/40 |
| 12,249,065 | B2 * | 3/2025 | Rittscher .................. | G06T 5/60 |
| 2012/0316421 | A1 * | 12/2012 | Kumar ............ | A61B 1/000096 |
| | | | | 600/407 |
| 2017/0053398 | A1 * | 2/2017 | Mahoor .................... | G06T 7/42 |
| 2018/0204046 | A1 * | 7/2018 | Bhattacharya ........ | G06F 18/217 |
| 2018/0253839 | A1 * | 9/2018 | Zur .................. | A61B 1/000094 |
| 2019/0205606 | A1 * | 7/2019 | Zhou ...................... | G06N 3/045 |
| 2019/0252073 | A1 * | 8/2019 | Hsu ........................ | G16H 30/40 |
| 2019/0303760 | A1 * | 10/2019 | Kumar .................. | G06N 3/045 |
| 2020/0069973 | A1 * | 3/2020 | Lou .......................... | G06N 5/04 |
| 2021/0142904 | A1 * | 5/2021 | Michuda ................ | G16H 50/20 |
| 2022/0031227 | A1 * | 2/2022 | Cho ...................... | G06N 3/0464 |
| 2022/0046166 | A1 * | 2/2022 | Holmstrom .......... | A61B 18/148 |
| 2022/0114415 | A1 | 4/2022 | Chen et al. | |
| 2022/0180199 | A1 | 6/2022 | Xu et al. | |
| 2022/0265360 | A1 * | 8/2022 | Jiang ...................... | G06V 10/82 |
| 2023/0342912 | A1 * | 10/2023 | He ......................... | G06T 7/0012 |
| 2024/0070858 | A1 * | 2/2024 | Zhang .................. | G06V 10/764 |
| 2024/0378735 | A1 * | 11/2024 | Taruttis ................ | A61B 1/0005 |
| 2024/0394890 | A1 * | 11/2024 | Zeng ........................ | G06T 7/11 |
| 2025/0079011 | A1 * | 3/2025 | Singh .................... | G16H 10/40 |
| 2025/0356486 | A1 * | 11/2025 | Pao ...................... | G06V 20/698 |

OTHER PUBLICATIONS

International Search Report and Written Opinion of PCT application No. PCT/CN2024/093190 issued from the International Search Authority on May 14, 2024.

* cited by examiner

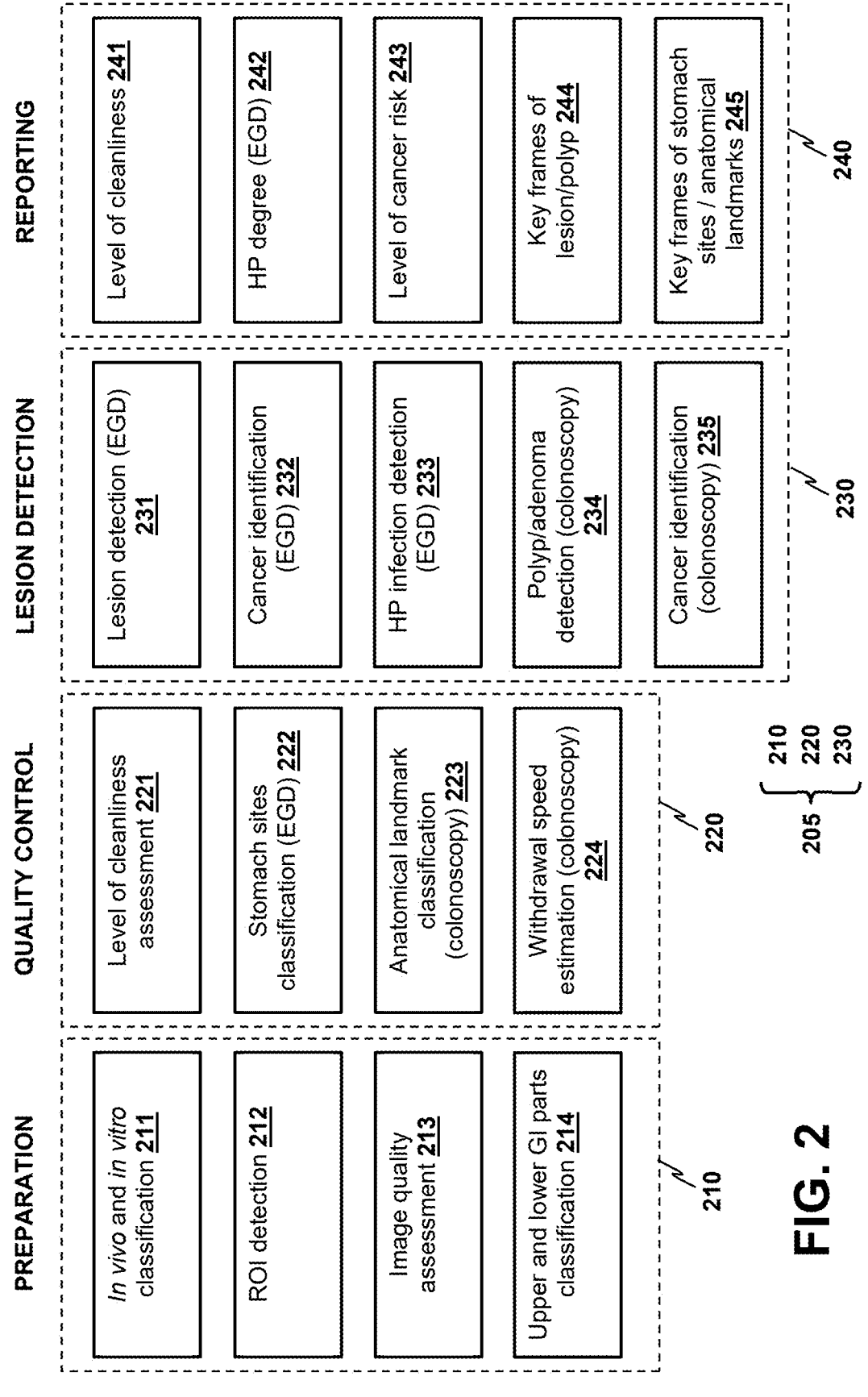

PREPARATION

*In vivo* and *in vitro* classification 211

ROI detection 212

Image quality assessment 213

Upper and lower GI parts classification 214

210

QUALITY CONTROL

Level of cleanliness assessment 221

Stomach sites classification (EGD) 222

Anatomical landmark classification (colonoscopy) 223

Withdrawal speed estimation (colonoscopy) 224

220

LESION DETECTION

Lesion detection (EGD) 231

Cancer identification (EGD) 232

HP infection detection (EGD) 233

Polyp/adenoma detection (colonoscopy) 234

Cancer identification (colonoscopy) 235

230

REPORTING

Level of cleanliness 241

HP degree (EGD) 242

Level of cancer risk 243

Key frames of lesion/polyp 244

Key frames of stomach sites / anatomical landmarks 245

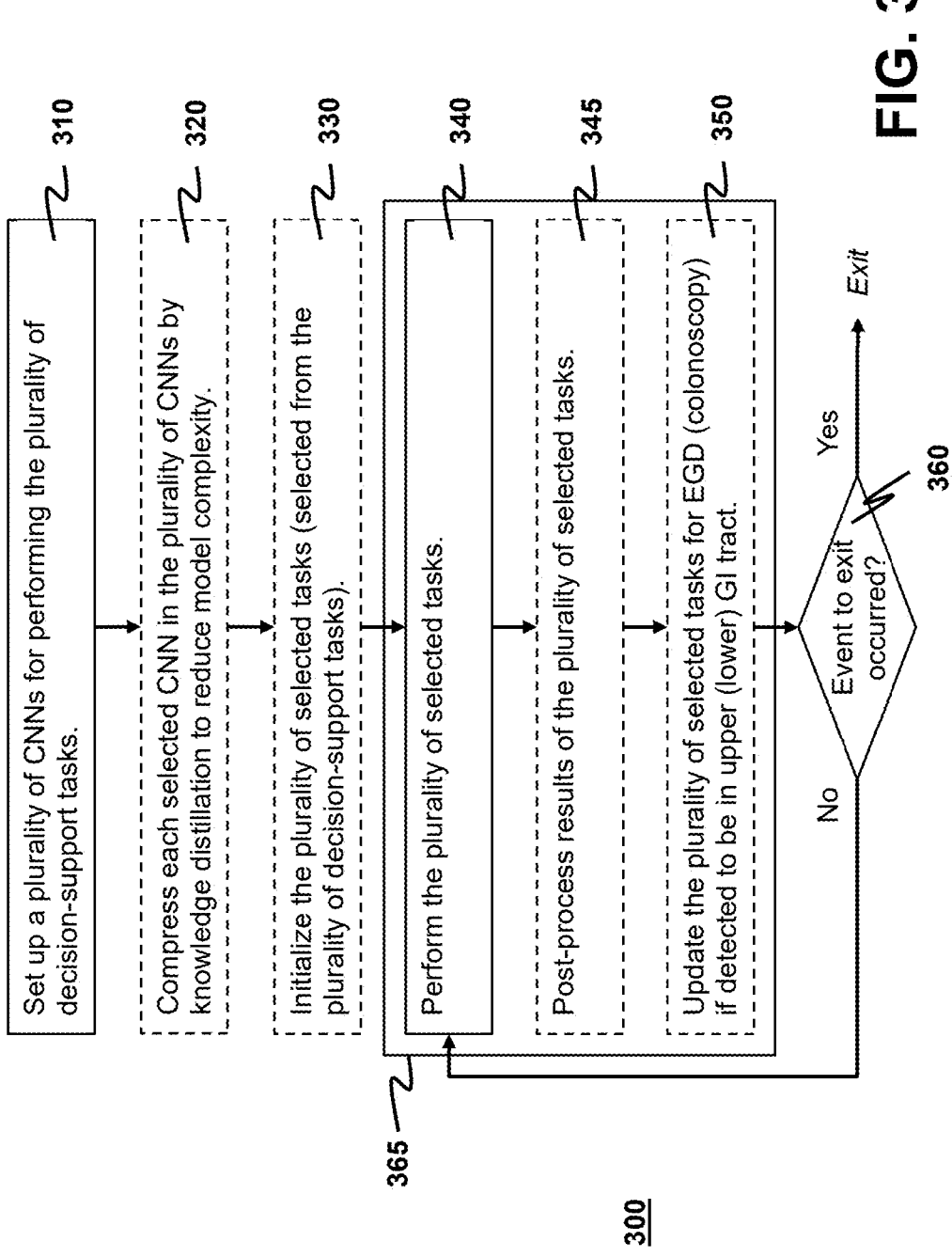

Set up a plurality of CNNs for performing the plurality of decision-support tasks. — 310

Compress each selected CNN in the plurality of CNNs by knowledge distillation to reduce model complexity. — 320

Initialize the plurality of selected tasks (selected from the plurality of decision-support tasks). — 330

Perform the plurality of selected tasks. — 340

Post-process results of the plurality of selected tasks. — 345

Update the plurality of selected tasks for EGD (colonoscopy) if detected to be in upper (lower) GI tract. — 350

Event to exit occurred? — 360

Yes → Exit

Table 1. Classification comparison.

| Model | Kernel IDs | Param. (M) | File size (MB) | MACs (G) | PyTorch Latency (ms) | QA Colon mean Acc. (%) | UGI 26-site mean Acc. (%) |
|---|---|---|---|---|---|---|---|
| ResNet18 | None | 11.2 | 43.8 | 1.62 | 1.45 | 92.1 | 91.38 |
| ResNet18+SKL | [1, 7, 9, 10, 11] | 1.95 | 5.7 | 0.52 | 1.0 | 92.9 | 91.23 |

Note: ResNet18 is revised with the SKL layers; On single RTX 2080Ti; Inference time (latency) benchmarked with torch.profiler; Image size: 384 x 384.

Table 2. Detection comparison.

| Model | Kernel IDs | Param. (M) | File size (MB) | MACs (G) | PyTorch Latency (ms) | mAP@0.5 (PennFudan) |
|---|---|---|---|---|---|---|
| RetinaNet | N/A | 30.5 | 119.1 | 10.4 | 6.4 | 0.943 |
| RetinaNet + SKL | [1, 2, 6] | 20.7 | 81.0 | 5.6 | 3.8 | 0.956 |
|  | [1, 7, 9, 10, 11] | 20.7 | 81.0 | 5.5 | 3.2 | 0.936 |

Note: The backbone is ResNet18; RetinaNet is revised with the SKL layers; On single RTX 2080Ti; Inference time (latency) benchmarked with torch.profiler; Image size: 384 x 384.

Table 3. Segmentation comparison.

| Model | Down Path Kernels | Up Path Kernels | Param. (M) | File size (MB) | MACs (G) | PyTorch latency (ms) | Ulcer Segmentation (DICE) |
|---|---|---|---|---|---|---|---|
| UNet | N/A | N/A | 31.0 | 121.3 | 123.1 | 16.3 | 0.781 |
| UNet+SKL | [1, 7, 9, 10, 11] | [1, 7, 9, 10, 11] | 6.0 | 23.6 | 36.2 | 9.8 | 0.811 |

Note: Unet is revised with SKL layers; On single RTX 2080Ti; Inference time (latency) benchmarked with torch.profiler; Image size: 384 x 384.

FIG. 6

Knowledge distillation for Image Quality Assessment 213

Table 4. IQA results of EGD.

| | Top-1* | Params | FLOPs | Model Size |
|---|---|---|---|---|
| ResNet18 | 94.33% | 11.20M | 3.22G | 44.80MB |
| ResNet34 (Teacher) | 94.17% | 21.8M | 3.68G | 83MB |
| ResNet18 (Student) | 94.89% | 11.20M | 3.22G | 44.80MB |

Table 5. IQA results of colonoscopy.

| | Top-1* | Params | FLOPs | Model Size |
|---|---|---|---|---|
| ResNet18 | 93.05% | 11.20M | 3.22G | 44.80MB |
| ResNet34 (Teacher) | 93.33% | 21.8M | 3.68G | 83MB |
| ResNet18 (Student) | 94.44% | 11.20M | 3.22G | 44.80MB |

Table 6. Polyp detection comparison.

| Models | Validation set: AP50 | Test set: AP50 |
|---|---|---|
| YOLOv5x (teacher) | 78.0% | 82.6% |
| YOLOv5s (student) | 69.3% | 76.7% |
| YOLOv5s + KD multi-head (3 layers) | 73.8% (+4.5) | 79.5% (+2.8) |
| YOLOv5s + KD multi-head (1 layer) | 71.2% (+1.9) | 77.9% (+1.2) |

FIG. 9

Table 7. Performance Evaluation for Multi-Task Model Sharing.

| Methods | Accuracy (task1, task2) | Param (M) | Inference time (ms) | File size. |
|---|---|---|---|---|
| ResNet18 (task 1, task 2) | 94.33%, 93.05% | 22.4 | 3.66 | 89.6 |
| MTAN (ResNet18) | 94.44%, 92.39% | 18.4 | 4.47 | 73.7 |
| HPS (ResNet18) | 93.83%, 93.0% | 11.2 | 2.18 | 44.8 |

Task 1:    The task 221 of Image cleanliness assessment for EGD.
Training data: 31621 images
Testing data: 1800 images

Task 2:    The task 221 of Image cleanliness assessment for colonoscopy.
Training data: 41018 images
Testing data: 1800 images

FIG. 12

Note.  BN: batch normalization
GELU: Gaussian error linear unit
DW: depth-wise
Conv: convolution
FFN: feed forward network

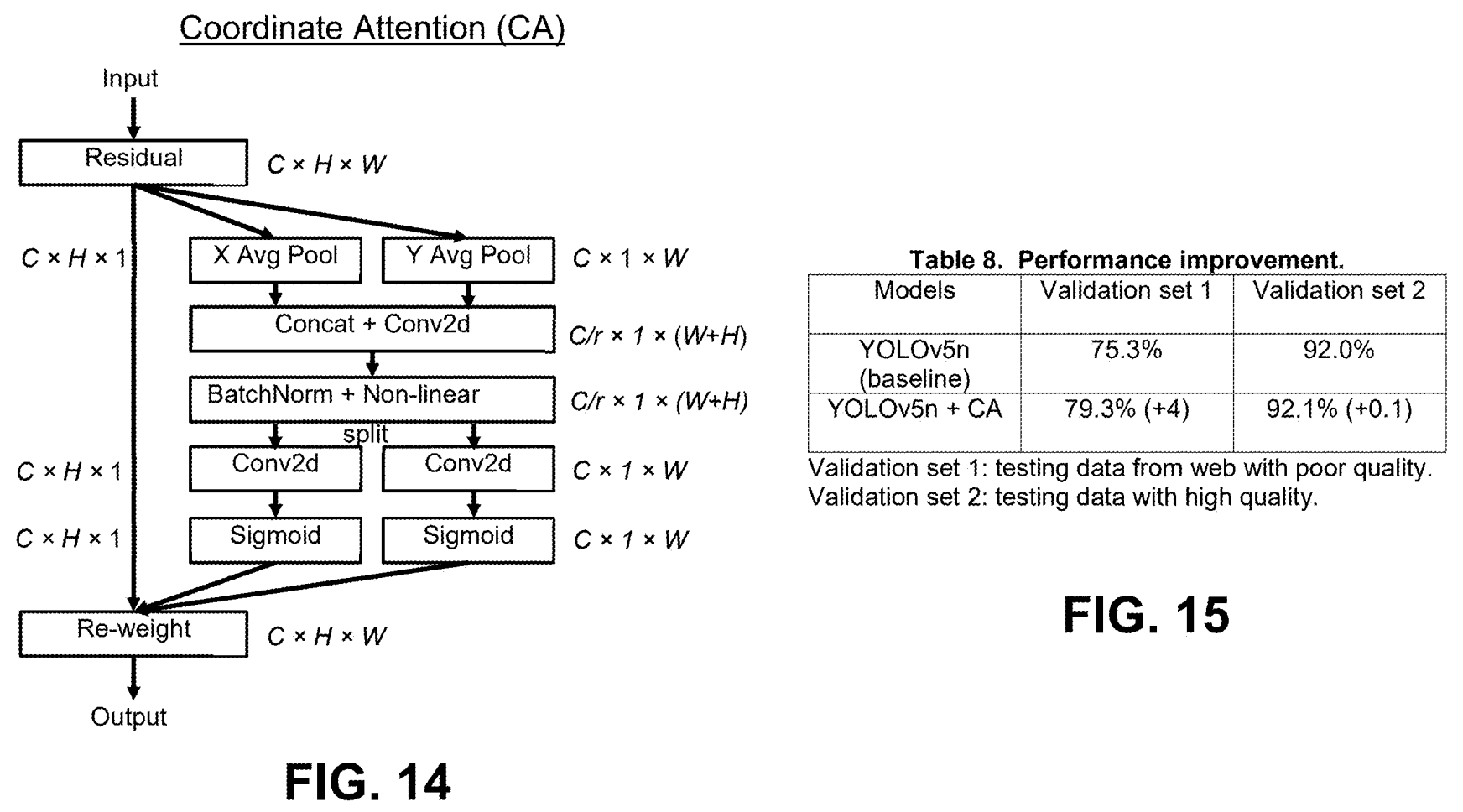

Table 8. Performance improvement.

| Models | Validation set 1 | Validation set 2 |
|---|---|---|
| YOLOv5n (baseline) | 75.3% | 92.0% |
| YOLOv5n + CA | 79.3% (+4) | 92.1% (+0.1) |

Validation set 1: testing data from web with poor quality.
Validation set 2: testing data with high quality.

FIG. 15

Coordinate Attention (CA)

FIG. 14

PORTABLE EDGE AI-ASSISTED DIAGNOSIS AND QUALITY CONTROL SYSTEM FOR GASTROINTESTINAL ENDOSCOPY

LIST OF ABBREVIATIONS

| | |
|---|---|
| AI | artificial intelligence |
| CA | coordinate attention |
| CNN | convolutional neural network |
| EGD | esophagogastroduodenoscopy |
| GI | gastrointestinal |
| GPU | graphics processing unit |
| HP | helicobacter pylori |
| HPS | hard parameter sharing |
| KD | knowledge distillation |
| IQA | image quality assessment |
| LKA | large kernel attention |
| MTAFN | multi-task attention fusion network |
| ROI | region of interest |
| SKL | Simplified Kernel Learning |
| VAN | visual attention network |
| ViT | visual transformer |

TECHNICAL FIELD

The present disclosure relates to a decision-support system for AI-assisted diagnosis and quality control in GI endoscopy, where the decision-support system is realized as an edge computing system, preferably portable.

BACKGROUND

There is an increasing demand on conducting GI endoscopic examinations for early detection and in treatment of GI cancers, such as gastric (stomach) cancer and colorectal cancer, in order to improve survival rates of patients. Lesion detection and quality control are two core parts in AI-assisted systems of GI endoscopy. The quality-control part is used to (a) minimize the occurrence of missed lesion detections in endoscopic examinations, and (b) reduce false positives of AI predictions. In a GI endoscopic examination, an endoscopist operates an endoscope to capture a sequence of GI endoscopic images of a subject. The captured sequence of images is processed by a decision-support system for lesion detection and quality control. Real-time analysis results on lesion detection and quality control are usually displayed. The endoscopist uses the real-time analysis results to make subsequent decisions in operating the endoscope and carrying out the rest of the examination. Note that it is essential that the decision-support system is capable of providing real-time analysis on the captured sequence of GI endoscopic images.

AI-based techniques for these two core parts are increasingly deployed because using these techniques reduces workload and pressure of medical staff. However, computation resources required in implementing a decision-support system for GI endoscopy are huge because: multiple tasks in the two core parts are required to be executed; the tasks are often concurrently executed; and large, complex machine-learning models are usually employed to perform these tasks in order to achieve a good performance in high-quality real-time detection of lesions as well as to flexibly adapt to different application scenarios. Also note that in order to achieve a better performance, the complexity of state-of-the-art models with respect to parameters is exponentially increasing.

A cloud-based server generally has a lot of computation resources. Building the decision-support system with the cloud-based server, however, is plagued with a need to build a high-capacity low-delay communication link for transferring a large file of endoscopic image data from an endoscope end of the system to the cloud-based server. In practice, most often it is difficult to guarantee low delay and high availability of the communication link. It is, however, not acceptable if the endoscopist receives results on lesion detection and quality control with a long delay, or if there is a network issue/breakdown that causes the cloud-based server unable to work. Alternatively, low delay is achievable by building the system with an edge computer, which is located near a site of conducting the GI endoscopic examination. Apart from this advantage, other advantages include a small size of the resultant decision-support system, a low cost, a low power consumption, and a reduced chance of leakage of patient's private information. The main drawback of using the edge computer in implementing the decision-support system is that the edge computer has limited computation resources as compared to desktop computers or servers with GPUs. It is desirable to implement the decision-support system on the edge computer while addressing the problem of limitation in computation resources.

U.S. Pat. No. 11,633,084 B2 discloses an image diagnosis assistance apparatus for assisting diagnosis of an endoscopic image. The disclosed apparatus uses a CNN for lesion detection, and is targeted for both EGD and colonoscopy. However, no quality-control algorithm is disclosed. The disclosed apparatus is also not specifically designed for implementation with an edge computer.

WO 2020215593 A1 discloses a system employing an AI-based technique of automatically evaluating quality of GI endoscopy according to images captured in an endoscopic examination. A plurality of quality indices is defined and used in the quality evaluation. Similar to U.S. Pat. No. 11,633,084 B2, the disclosed system is not specifically designed for implementation with an edge computer.

There is a need for an AI-based decision-support system used in GI endoscopy and implemented by one or more edge computers, where the system performs lesion detection and quality control on a sequence of GI endoscopic images.

SUMMARY

A first aspect of the present disclosure is to provide a decision-support system for GI endoscopy.

The system comprises one or more computers configured to execute a computing process for processing a sequence of endoscopic images acquired in a GI endoscopic examination to at least perform a plurality of selected tasks dynamically selected from a plurality of decision-support tasks. The computing process comprises: setting up a plurality of CNNs for performing the plurality of decision-support tasks according to the sequence of endoscopic images, an individual CNN being modeled with one or more learnable kernels, wherein each learnable kernel used in the plurality of CNNs is modeled as a linear combination of a set of fixed kernels with the set of fixed kernels being invariant over the plurality of CNNs so as to simplify kernel learning in comparison to training a conventional CNN model with unrestricted one or more kernels to thereby reduce a computation-resource requirement of the one or more computers and hence enable the decision-support system to be realized as an edge computing system near a site of performing the GI endoscopic examination; executing a subprocess, wherein the subprocess comprises performing the plurality of selected tasks by processing the sequence of endoscopic images with each CNN in a plurality of selected CNNs, wherein the plurality of selected CNNs is identified from the plurality of CNNs and is used for performing the plurality of selected tasks; and repeating the subprocess until an event indicative of exiting from looping the subprocess occurs.

In certain embodiments, the subprocess further comprises post-processing results generated from performing the plurality of selected tasks.

In certain embodiments, each kernel in the set of fixed kernels is a 3×3 matrix.

In certain embodiments, the computing process further comprises compressing an individual selected CNN in the plurality of selected CNNs by knowledge distillation to reduce a model complexity of the individual selected CNN such that the individual selected CNN as compressed is used to process the sequence of endoscopic images to perform one or more corresponding decision-support tasks associated with the individual selected CNN to thereby further reduce the computation-resource requirement of the one or more computers.

The plurality of CNNs may include one or more multi-task CNNs. An individual multi-task CNN is used for performing plural corresponding decision-support tasks in the plurality of decision-support tasks. In one embodiment of the setting up of the plurality of CNNs, at least one multi-task CNN is formed with one or more layers shared by the plural corresponding decision-support tasks to thereby further reduce the computation-resource requirement of the one or more computers. In another embodiment of the setting up of the plurality of CNNs, at least one multi-task CNN is formed with a serial cascade of multi-task attention fusion networks to thereby further reduce the computation-resource requirement of the one or more computers.

In certain embodiments, the plurality of decision-support tasks is partitioned into a first plurality of tasks performed in EGD, a second plurality of tasks performed in colonoscopy, and a third plurality of tasks performed in both EGD and colonoscopy. The third plurality of tasks includes the task of determining an imaging location in an upper or lower GI tract so as to determine whether EGD or colonoscopy is carried out. In addition, the computing process further comprises initializing the plurality of selected tasks as the third plurality of tasks before an initial execution of the subprocess. The subprocess further comprises: if the imaging location is determined to be in the upper GI tract during performing the plurality of selected tasks, then updating the plurality of selected tasks by including the first plurality of tasks and removing the second plurality of tasks; and if the imaging location is determined to be in the lower GI tract during performing the plurality of selected tasks, then updating the plurality of selected tasks by including the second plurality of tasks and removing the first plurality of tasks, whereby the updating of the plurality of selected tasks from time to time provides automatic configuration of the decision-support system for EGD and colonoscopy.

In certain embodiments, the plurality of decision-support tasks includes a plurality of preparation tasks, a plurality of quality-control tasks and a plurality of lesion-detection tasks. The plurality of preparation tasks includes tasks of: classifying an imaging location as an in vivo location or an in vitro one; detecting a ROI on an image captured at the imaging location; assessing an image quality achieved at the imaging location; and determining the imaging location in an upper or lower GI tract so as to determine whether EGD or colonoscopy is carried out. The plurality of quality-control tasks includes tasks of: assessing a level of cleanliness at the imaging location; classifying a stomach site in EGD; classifying an anatomical landmark at the imaging location in colonoscopy; and estimating a withdrawal speed in colonoscopy. The plurality of lesion-detection tasks includes tasks of: detecting a lesion in EGD; identifying a cancer in EGD; detecting HP infection in EGD; detecting polyp/adenoma in colonoscopy; and identifying a cancer in colonoscopy.

In certain embodiments, the anatomical landmark is classified as a terminal ileum, a cecum, an ascending colon, a traverse colon, a descending colon, a sigmoid colon, a rectum, or an anus.

In certain embodiments, the computing process further comprises performing one or more reporting tasks selected from tasks of: reporting the assessed level of cleanliness; reporting a HP degree in EGD; reporting a level of cancer risk; reporting key images of lesion/polyp as extracted from the sequence of endoscopic images; and reporting key images of stomach sites/anatomical landmarks as extracted from the sequence of endoscopic images.

In certain embodiments, the plurality of decision-support tasks includes a plurality of lesion-detection tasks. The plurality of lesion-detection tasks includes a task of detecting a lesion in EGD. In the setting up of the plurality of CNNs, a corresponding CNN associated with the task of detecting the lesion in EGD is a VAN.

In certain embodiments, the plurality of decision-support tasks includes a plurality of lesion-detection tasks. The plurality of lesion-detection tasks includes a task of detecting polyp/adenoma in colonoscopy. In the setting up of the plurality of CNNs, a corresponding CNN associated with the task of detecting polyp/adenoma in colonoscopy is a ViT utilizing CA.

In certain embodiments, the plurality of decision-support tasks includes a plurality of quality-control tasks. The plurality of quality-control tasks includes a task of classifying an anatomical landmark at an imaging location in colonoscopy. In the setting up of the plurality of CNNs, a corresponding CNN associated with the task of classifying the anatomical landmark at the imaging location in colonoscopy is a mutual learning-based model.

In certain embodiments, the plurality of decision-support tasks includes a plurality of quality-control tasks. The plurality of quality-control tasks includes a task of estimating a withdrawal speed in colonoscopy. In the setting up of the plurality of CNNs, a corresponding CNN associated with the task of estimating the withdrawal speed in colonoscopy is a mutual learning-based model.

In certain embodiments, the plurality of decision-support tasks includes a plurality of quality-control tasks and a plurality of lesion-detection tasks. The plurality of selected tasks includes one or more selected lesion-detection tasks and one or more selected quality-control tasks, where the one or more selected lesion-detection tasks are selected from the plurality of lesion-detection tasks, and the one or more selected quality-control tasks are selected from the plurality of quality-control tasks. The performing of the plurality of selected tasks comprises: buffering the sequence of endoscopic images with a first buffering scheme to yield a first buffered sequence of endoscopic images, the first buffered sequence being used for performing the one or more selected lesion-detection tasks, wherein the first buffering scheme is arranged to generate the first buffered sequence with a first latency that satisfies a first set of latency requirements required by the one or more selected lesion-detection tasks in receiving the sequence of endoscopic images; performing the one or more selected lesion-detection tasks to generate lesion-detection results, an input to the one or more selected lesion-detection tasks being the first buffered sequence; buffering the sequence of endoscopic images with a second buffering scheme to yield a second buffered sequence of endoscopic images, the second buffered sequence being used for performing the one or more selected quality-control tasks, wherein the second buffering scheme is arranged to generate the second buffered sequence with a second latency that satisfies a second set of latency requirements required by the one or more selected quality-control tasks in receiving the sequence of endoscopic images; and performing the one or more selected quality-control tasks to generate quality-control results, an input to the one or more selected quality-control tasks being the second buffered sequence. The subprocess further comprises post-processing results generated from performing the plurality of selected tasks. The post-processing of the generated results comprises integrating the lesion-detection results and quality-control results to generate one or more value-added results.

In certain embodiments, the one or more computers are implemented with one or more GPUs, and the first latency is lower than the second latency. The first buffering scheme uses a dropping mechanism in generating the first buffered sequence to achieve the first latency. The second buffering scheme uses dynamic batching inference in generating the second buffered sequence to increase an efficiency of GPU use in the one or more computers while achieving the second latency.

In certain embodiments, the one or more value-added results are selected from a group consisting of an estimated degree of cancer risk, a set of one or more identified representative lesions, a reminder of flushing water for improving quality of subsequently captured images, an estimated withdrawal speed in colonoscopy, and a set of one or more blind site spots identified missing in the sequence of endoscopic images in EGD.

In certain embodiments, the one or more computers are configured to receive a sequence of video frames as the sequence of endoscopic images.

In certain embodiments, each of the one or more computers is portable, and the decision-support system is configured to be portable.

In certain embodiments, the computing process further comprises performing one or more reporting tasks for reporting results obtained from performing the plurality of selected tasks. The decision-support system further comprises a display for visually displaying the obtained results.

A second aspect of the present disclosure is to provide a GI endoscopic system for conducting a GI endoscopic examination on a human subject. The GI endoscopic examination is of a type selected from EGD and colonoscopy.

The system comprises an endoscope for inspecting the human subject in the GI endoscopic examination to thereby yield a sequence of endoscopic images. The endoscope is configured to perform the GI endoscopic examination of the selected type. Particularly, the GI endoscopic system further comprises any of the embodiments of the disclosed decision-support system for processing the sequence of endoscopic images.

Other aspects of the present disclosure are disclosed as illustrated by the embodiments hereinafter.

BRIEF DESCRIPTION OF THE DRAWINGS

FIG. 2 provides exemplary lists of decision-support tasks and reporting tasks to be performed in the decision-support system.

FIG. 3 depicts a flowchart showing exemplary steps used in a computing process for processing a sequence of endoscopic images in the decision-support system.

FIG. 6 depicts Tables 1-3 for demonstrating advantages of the lightweight model in classification performance, detection performance and segmentation performance, respectively.

FIG. 9 depicts Tables 4-6 for demonstrating advantages of model compression via KD, where Tables 4 and 5 list the IQA results of EGD and of colonoscopy, respectively, and Table 6 lists comparison results on polyp detection among different CNN models.

FIG. 12 depicts Table 7 for demonstrating advantages of using multi-task CNNs to reduce model complexity, where Table 7 lists performance data of a multi-task CNN used for performing the tasks of image cleanliness assessment for EGD and for colonoscopy.

FIG. 14 depicts an example of CA usable in the decision-support system for enhancing robustness of lesion detection against a poor validation set.

FIG. 15 depicts Table 8 for demonstrating robustness of using a ViT utilizing CA in lesion detection against the presence of a validation set of poor quality.

Skilled artisans will appreciate that elements in the figures are illustrated for simplicity and clarity and have not necessarily been depicted to scale.

DETAILED DESCRIPTION

The present disclosure provides a decision-support system for GI endoscopy. The decision-support system provides AI-assisted diagnosis and quality control in GI endoscopy. Advantageously, the decision-support system is realizable as an edge computing system near a site of conducting a GI endoscopic examination. Furthermore, the system performs multi-tasks on edge devices with the aid of optimized models. Other advantages are given as follows. The system is targeted for both EGD and colonoscopy. It enables automatic and flexible configurations for multiple application scenarios. It provides seamless integration of lesion detection and quality control. In addition, the system is designed for edge devices.

Figure 1:
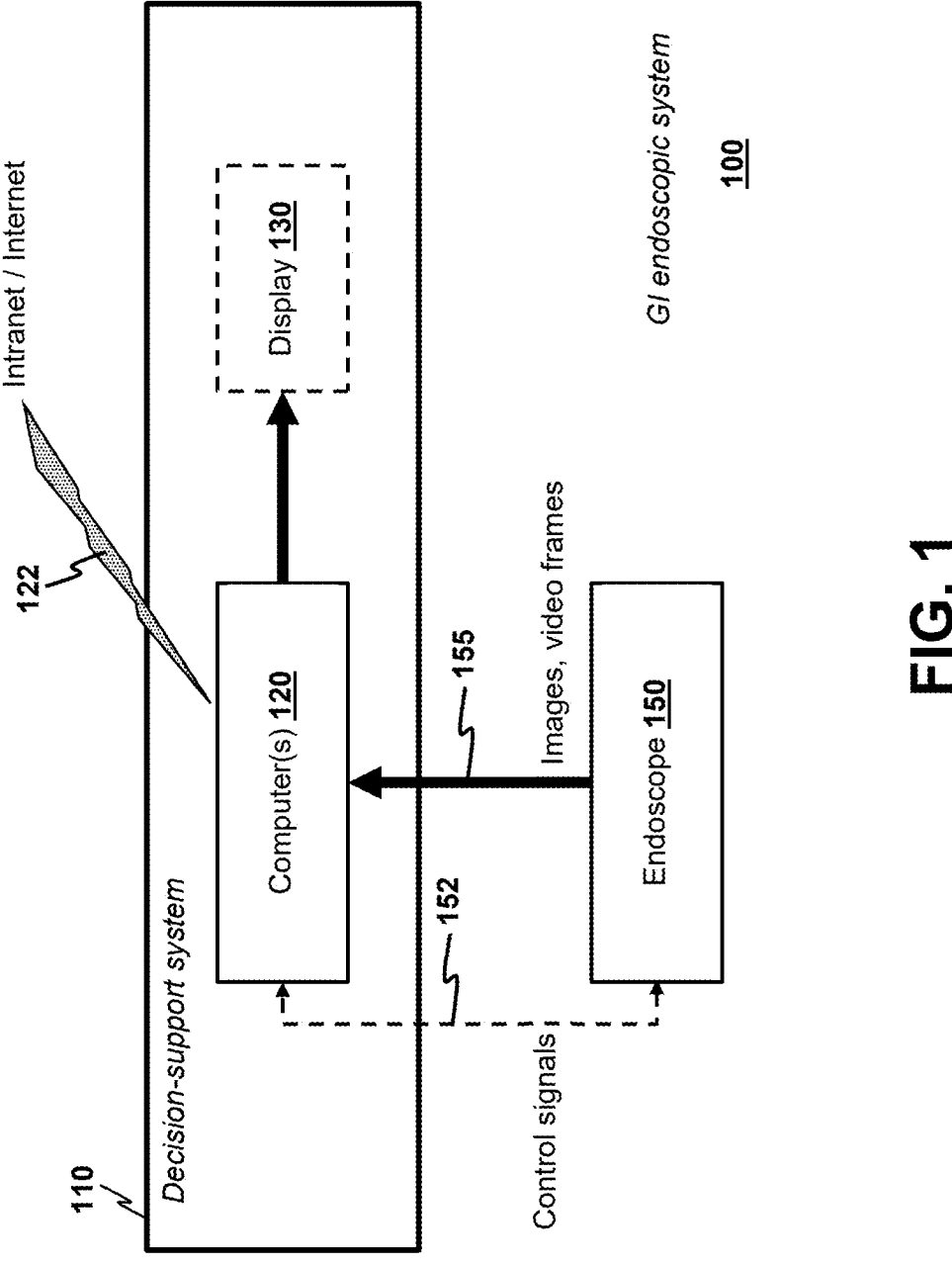
FIG. 1 depicts a schematic diagram of a GI endoscopic system formed with an exemplary decision-support system as disclosed herein for AI-assisted diagnosis and quality control, where the decision-support system is realized as an edge computing system.

Practically, the disclosed decision-support system is used in a GI endoscopic system, which is used by an endoscopist to perform GI endoscopy. FIG. 1 depicts a schematic diagram of a typical GI endoscopic system 100 for conducting a GI endoscopic examination on a human subject. The GI endoscopic examination is of a type selected from EGD and colonoscopy. The GI endoscopic system 100 comprises an endoscope 150, and an exemplary decision-support system 110 in accordance with various embodiments of the disclosed decision-support system. The endoscope 150 is used for inspecting the human subject in the GI endoscopic examination to thereby yield a sequence of endoscopic images 155, usually a sequence of video frames. The endoscope 150 is configured to perform the GI endoscopic examination of the selected type. That is, the endoscope 150 is an instrument designed to perform EGD or colonoscopy according to the selected type. The decision-support system 110 acquires the sequence of endoscopic images 155 as generated in the GI endoscopic examination. The decision-support system 110 includes one or more computers 120 to process the sequence of endoscopic images 155 to thereby generate results on lesion detection and quality control. Usually, the decision-support system 110 further includes a display 130 (e.g., a visual display unit) for reporting the generated results to the endoscopist. The goal of the present disclosure is to enable the one or more computers 120 to be realizable by a group of one or more edge computers such that the sequence of endoscopic images 155 needs not be real-time transmitted to a remote cloud-based server for generating the results. Preferably, each of the one or more computers 120 is portable, and the decision-support system 110 is configured to be portable as well. Usually, the one or more computers 120 are connectable to an intranet or the Internet through a wireless communication link 122. Optionally, control signals 152 are exchanged between the one or more computers 120 and the endoscope 150.

Exemplarily, the decision-support system 110 is realized with an algorithm framework composed of a plurality of AI-based algorithms for performing a plurality of decision-support tasks, and a plurality of routine algorithms for performing a plurality of reporting tasks. FIG. 2 provides exemplary lists of decision-support tasks and reporting tasks. By providing a wide variety of decision-support tasks, the decision-support system 110 can be easily and flexibly configured for different endoscopic applications to adapt itself to different needs.

The plurality of decision-support tasks (referenced as 205) includes a plurality of preparation tasks 210, a plurality of quality-control tasks 220 and a plurality of lesion-detection tasks 230. The plurality of lesion-detection tasks 230 is executed for detecting lesions from the sequence of endoscopic images 155 to thereby yield lesion-detection results. The plurality of quality-control tasks 220 is executed for measuring quality-control variables that determine reliability of the lesion-detection results to thereby yield quality-control results. The plurality of preparation tasks 210 consists of tasks intended to obtain environmental information when an endoscopic probe of the endoscope 150 is on the way to reach an object of interest (such as a tumor) in the GI tract of the human subject.

Exemplarily, the plurality of preparation tasks 210 includes: task 211 of classifying an imaging location as an in vivo location or an in vitro one; task 212 of detecting a ROI on an image captured at the imaging location; task 213 of assessing an image quality achieved at the imaging location; and task 214 of determining the imaging location in an upper or lower GI tract so as to determine whether EGD or colonoscopy is carried out. As used herein, the imaging location is a location at which the endoscopic probe captures an image. The imaging location may be inside or outside the GI tract of the human subject. The ROI is an area of image on which an object of interest in the GI tract is present. Specifically, the ROI detection is to crop off irrelevant image portion(s) from a raw endoscopic image that contains irrelevant parts such as black borders and patient information. Note that the raw image is much larger in size than the cropped-off portions. It is required to crop the irrelevant parts out for AI inference with the aid of ROI detection. Note that other preparation tasks as deemed appropriate by those skilled in the art according to practical situations under consideration may be included in the plurality of preparation tasks 210.

Exemplarily, the plurality of quality-control tasks 220 includes: task 221 of assessing a level of cleanliness at the imaging location; task 222 of classifying a stomach site in EGD; task 223 of classifying an anatomical landmark at the imaging location in colonoscopy; and task 224 of estimating a withdrawal speed in colonoscopy. Note that a low level of cleanliness of the GI tract due to incomplete bowel preparation avoids tissues of the GI tract to be completely and clearly imaged. Classifying the stomach site or anatomical landmark that the endoscopic probe comes across enables the decision-support system 110 to keep track of the navigated path of the endoscopic probe. Of interest in colonoscopy, the anatomical landmark may be classified as a terminal ileum, a cecum, an ascending colon, a traverse colon, a descending colon, a sigmoid colon, a rectum, or an anus. It is known that a positive advantage of increasing adenoma detection rates may be obtained by having longer withdrawal times in colonoscopy. Note that other quality-control tasks as deemed appropriate by those skilled in the art according to practical situations under consideration may be included in the plurality of quality-control tasks 220. These other quality-control tasks may include, for instance, blind spot monitoring and inspection time monitoring for EGD, and withdrawal speed/stability monitoring for colonoscopy.

Exemplarily, the plurality of lesion-detection tasks 230 includes: task 231 of detecting a lesion in EGD; task 232 of identifying a cancer in EGD; task 233 of detecting HP infection in EGD; task 234 of detecting polyp/adenoma in colonoscopy; and task 235 of identifying a cancer in colonoscopy. Types of the lesion for detection in the task 231 may include, but are not limited to, cancerous lesion, ulcerated lesion, benign polyp and tumor-like lesion. Types of the polyp/adenoma for detection in the task 234 may include, but are not limited to, adenomatous polyp and hyperplastic polyp. Note that other lesion-detection tasks as deemed appropriate by those skilled in the art according to practical situations under consideration may be included in the plurality of lesion-detection tasks 230.

The plurality of reporting tasks (referenced as 240) may include: task 241 of reporting the assessed level of cleanliness; task 242 of reporting a HP degree in EGD; task 243 of reporting a level of cancer risk; task 244 of reporting key images of lesion/polyp as extracted from the sequence of endoscopic images 155; and task 245 of reporting key images of stomach sites/anatomical landmarks as extracted from the sequence of endoscopic images 155.

Exemplarily, the one or more computers 120 in the decision-support system 110 are configured to execute a computing process for processing the sequence of endoscopic images 155 acquired in the GI endoscopic examination to at least perform a plurality of selected tasks dynamically selected from the plurality of decision-support tasks 205. FIG. 3 depicts a flowchart showing exemplary steps used in the computing process (referenced as 300).

AI-based techniques are used for performing the plurality of decision-support tasks 205. Although in an actual operation, only the plurality of selected tasks in the plurality of decision-support tasks 205 is performed, it is desirable, as a preparatory step, to prepare for the plurality of decision-support tasks 205 rather than to prepare only for the plurality of selected tasks.

In an initialization step 310, a plurality of CNNs for performing the plurality of decision-support tasks 205 according to the sequence of endoscopic images 155 is set up. An individual CNN in the plurality of CNNs is modeled with one or more learnable kernels. The individual CNN may be a pre-trained one or an untrained CNN. Preferably, the step 310 includes a procedure of training the untrained CNN so as to ensure that all CNNs in the plurality of CNNs are trained before proceeding to other steps in the computing process 300.

Generally, a typical CNN is formed by a serial cascade of plural convolutional layers followed successively by a flatten layer, a fully-connected layer and then an activation function to generate an output. The convolutional layers contain feature maps. Feature maps of a convolutional layer are convolved with respective kernels to form feature maps of a next convolutional layer. Each kernel is a two-dimensional array of data. The data in the two-dimensional array are learnt in training. Similarly, an input image is convolved with respective kernels to form feature maps of the first convolutional layer. Note that each convolutional layer typically contains plural channels. For two successive convolutional layers, if the first layer has $N_1$ channels and the second one has $N_2$, the number of kernels involved in computation of feature maps of the second layer from feature maps in the first layer is $N_1 \times N_1$.

Figure 4:
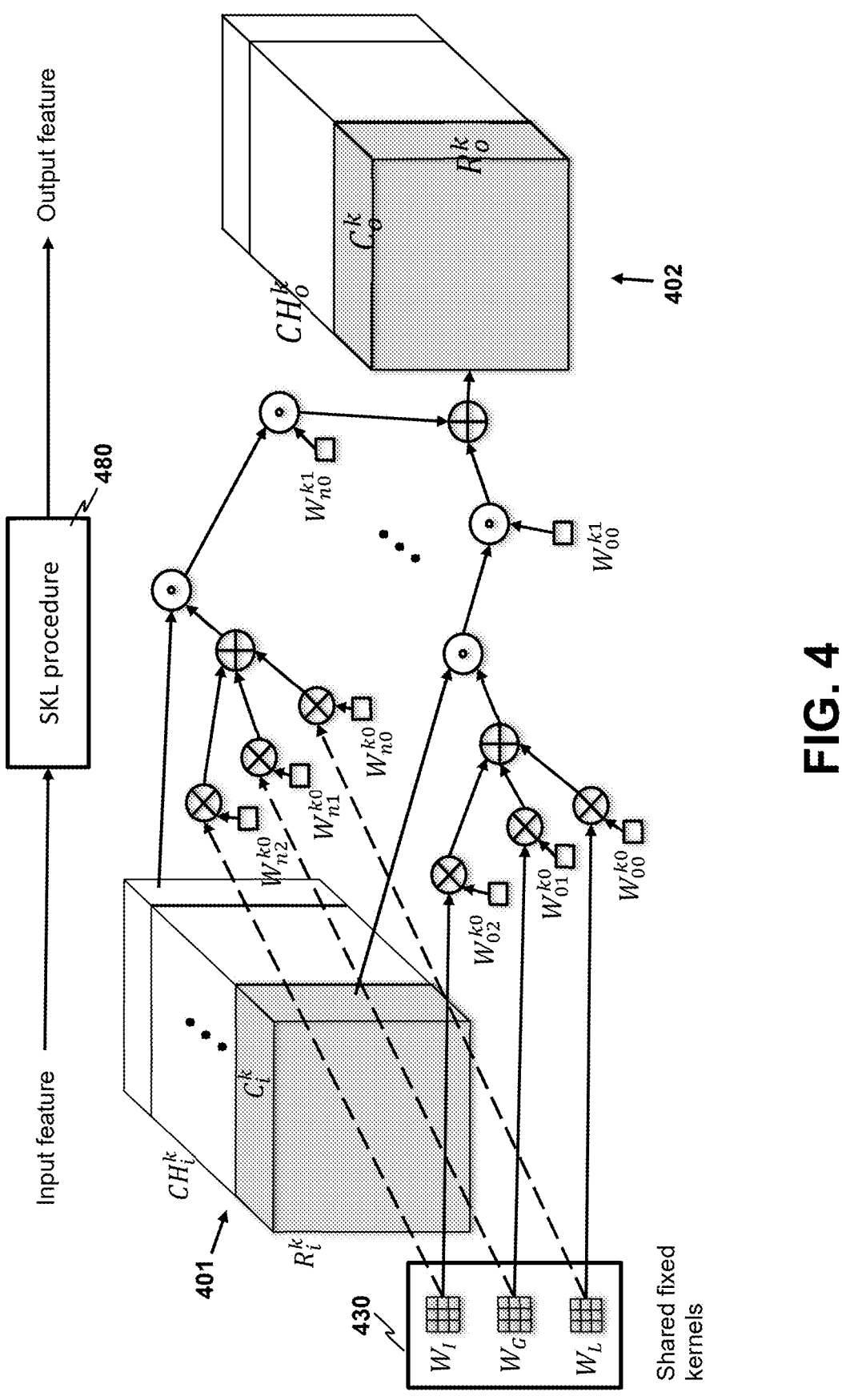
FIG. 4 depicts an example showing generation of feature maps of a second convolutional layer from feature maps of a first convolutional layer with kernels each of which is a linear combination of a set of key, fixed kernels.

The Inventors have observed that using a lightweight model of learnable kernels in setting up the plurality of CNNs reduces a computation-resource requirement of the one or more computers 120. The lightweight model is herein coined as Simplified Kernel Learning (SKL). Generally, computation resources of the one or more computers 120 include an amount of computing power and a size of memories available for use. The amount of computing power may be measured by, e.g., the number of floating point operations per second. In conventional deep learning models, kernels are learned through samples. Each kernel could be in forms of thousands of combinations. However, the Inventors have observed that, in traditional computer vision techniques, practically only a small number of common kernels are used. Inspired by this observation, the Inventors have investigated an approach of combining several key kernels that are typical into a learnt kernel. The learnt kernel is combined by the weights adjusted by a learning process of CNN with input samples. These key kernels are common and shared among layers, thus saving the memory of the one or more computers 120. FIG. 4 depicts an example showing generation of feature maps of a second convolutional layer 402 from feature maps of a first convolutional layer 401 with kernels each generated as a linear combination of a set of fixed kernels 430 ($W_L$, $W_G$, $W_J$). Weights used in respective linear combinations are determined by a SKL procedure 480.

Figure 5:
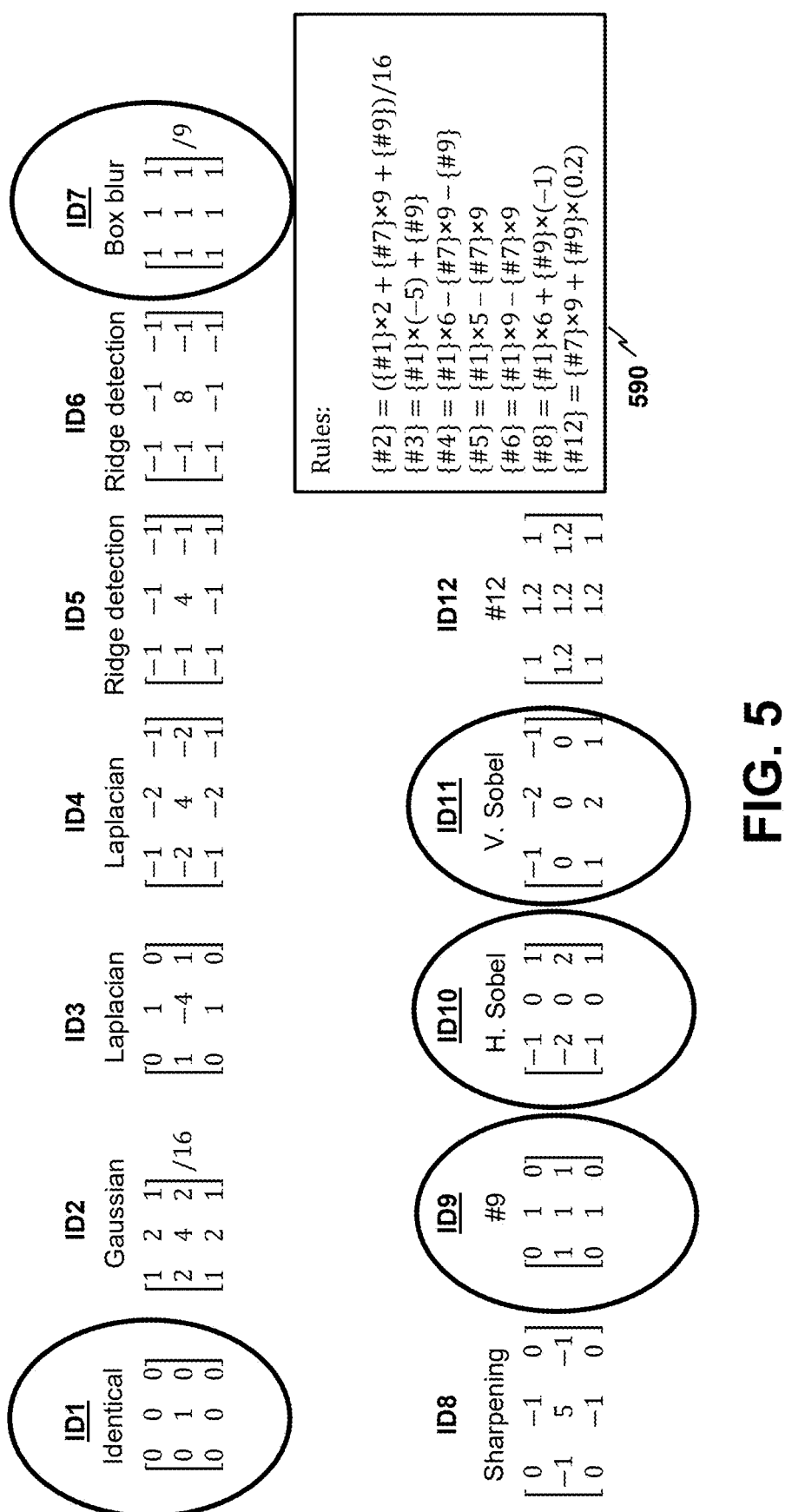
FIG. 5 provides an illustrative example of selecting the set of key, fixed kernels for a lightweight model of learnable kernels used in a CNN.

The key-kernel selection is based on analysis and experiments. FIG. 5 provides an illustrative example of selecting the key kernels. First, a plurality of prototype filters each being a 3×3 matrix is used. Although in FIG. 5, each of the prototype filters is a 3×3 matrix, matrices of other orders (such as 4×4 and 8×8) may also be used. The plurality of prototype filters respectively performs: an identity (no change) operation ID1; a Gaussian filtering operation ID2; a first Laplacian filtering operation ID3; a second Laplacian filtering operation ID4; a first ridge-detection operation ID5; a second ridge-detection operation ID6; a box blurring operation ID7; a sharpening operation ID8; a first ad hoc filtering operation ID9; a first Sobel filtering operation along a horizontal direction ID10; a second Sobel filtering operation along a vertical direction ID11; and a second ad hoc filtering operation ID12. Some of the prototype filters are derived from others. An inset 590 in FIG. 5 shows some relationships among the operations ID1-ID12. It is apparent that the matrices ID1, ID7, ID9, ID10 and ID11 are fundamental matrices such that each of the remaining matrices ID2-ID6, ID8 and ID12 is generated by a linear combination of the fundamental matrices. The lightweight model is that each learnable kernel in the form of a matrix is a linear combination of a set of fundamental matrices that are fixed, i.e. {ID1, ID7, ID9, ID10, ID11}. A CNN layer that uses the lightweight model in kernel selection has a much smaller number of parameters, thus requiring less computation resources and leading to less latency. Such advantages are demonstrated in Tables 1, 2 and 3, which compare performances with and without using SKL in classification, detection and segmentation, respectively. Tables 1-3 are depicted in FIG. 6.

In the initialization step 310, each learnable kernel used in the plurality of CNNs is advantageously modeled as a linear combination of a set of fixed kernels. The set of fixed kernels corresponds to the set of fundamental matrices that are fixed as mentioned above. Furthermore, the set of fixed kernels is invariant over the plurality of CNNs. Generating respective learnable kernels in the plurality of CNNs based on the set of fixed kernels simplifies kernel learning in comparison to training a conventional CNN model with unrestricted one or more kernels. It thereby reduces a computation-resource requirement of the one or more computers 120 and hence enables the decision-support system 110 to be realized as an edge computing system near a site of performing the GI endoscopic examination.

As demonstrated in FIG. 5, each fixed kernel in the set is selected to be a matrix having an order as low as 3×3. This choice of low order in modeling each fixed kernel enables a large reduction of required computation resources for the one or more computers 120. Other choices of matrix order can also be used.

After the plurality of CNNs is set up in the step 310, it is intended that the plurality of selected tasks is performed in step 340, and that the step 340 is repeated for continuing to provide decision-support information or advice to the endoscopist. In the step 340, the sequence of endoscopic images 155 is processed with each CNN in a plurality of selected CNNs to perform the plurality of selected tasks. The plurality of selected CNNs is identified from the plurality of CNNs and is used for performing the plurality of selected tasks.

In realizing the repeated execution of the step 340, a subprocess 365 is set up in the computing process 300. The subprocess 365 comprises the step 340. In step 360, the subprocess 365 is repeated until an event indicative of exiting from looping the subprocess 365 occurs. Such event includes, for example, that: the task 211 detects exit of the endoscopic probe from the body of the human subject to the outside; and the IQA task 213 finds that the sequence of endoscopic images 155 is unacceptably poor in image quality. Although looping the subprocess 365 is terminated, the present disclosure is not restricted that looping a new instance of the subprocess 365 will not be established in the computing process 300 in a later stage. For instance, a new instance of the subprocess 365 is set up after the IQA task 213 finds that the sequence of endoscopic images 155 has an unacceptably poor quality, where the new instance of the subprocess 365 includes the plurality of preparation tasks 210 but excludes the plurality of lesion-detection tasks 230 and the plurality of quality-control tasks 220.

Optionally, the subprocess 365 further includes step 345 of post-processing results generated from the step 340 of performing the plurality of selected tasks. More details of the step 345 will be provided later.

The computation-resource requirement of the one or more computers 120 may be further reduced by utilizing KD for model compression. KD may generally be applied to any CNN in the plurality of CNNs such that respective decision-support tasks in the plurality of decision-support tasks 205 may be benefited from KD. For illustration, FIGS. 7 and 8 depict procedures of KD in model compression for first and second CNNs used to accomplish the task 213 of IQA and the task 234 of polyp detection, respectively.

Figure 7:
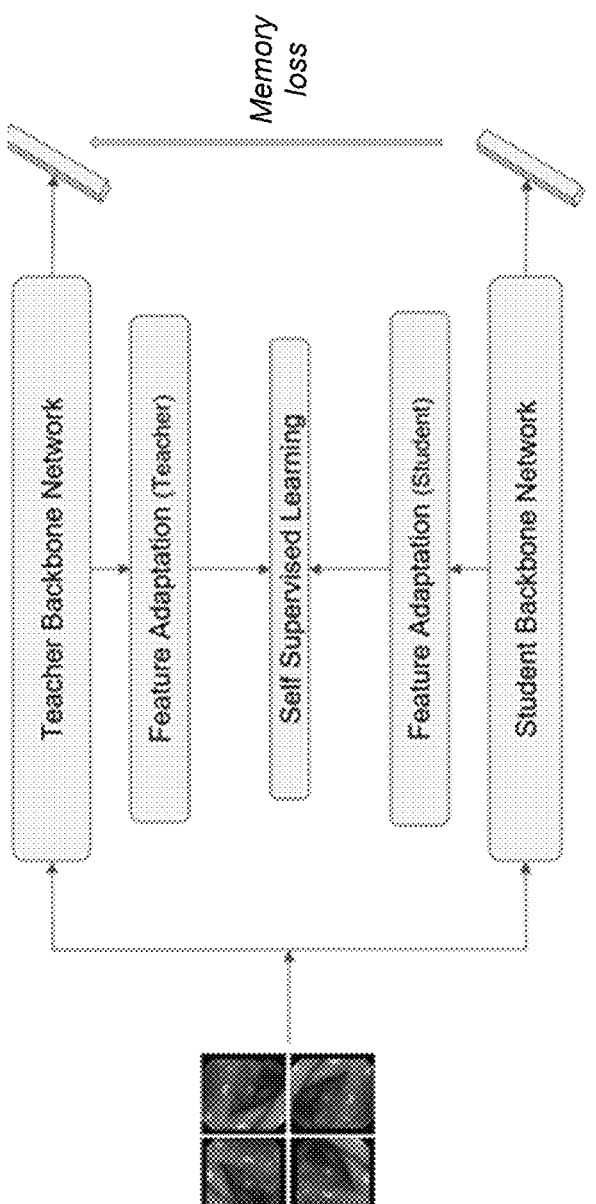
FIG. 7 depicts, for illustration, a knowledge-distillation procedure for model compression of a CNN used to accomplish a decision-support task of IQA.
Figure 8:
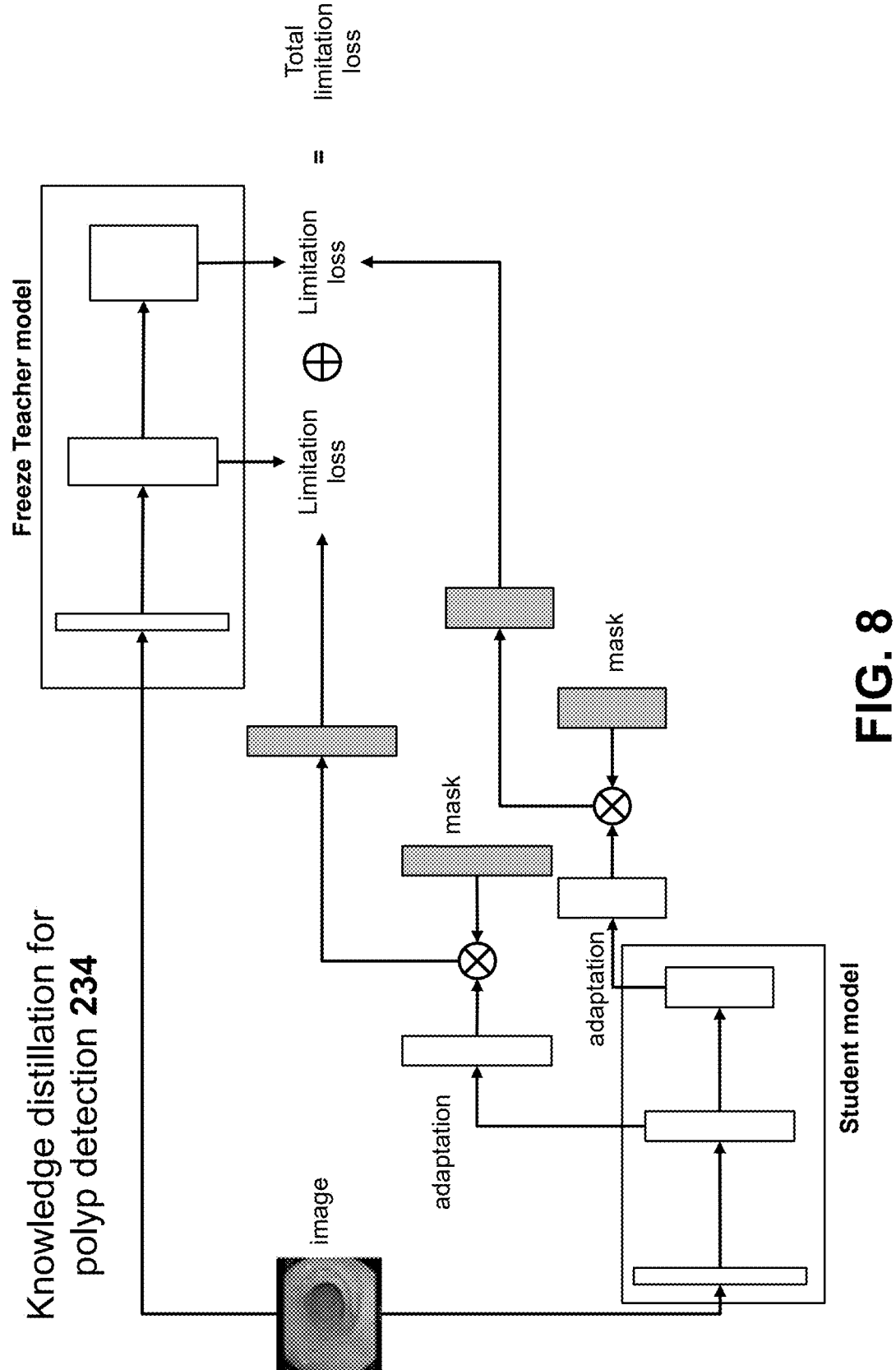
FIG. 8 depicts, for illustration, a knowledge-distillation procedure for model compression of a CNN used to accomplish a decision-support task of polyp detection.

As shown in FIG. 7, both teacher and student networks are equipped with several auxiliary classifiers after various convolutional stages to capture diverse self-supervised augmented knowledge from hierarchical feature maps during training. While inference of the student network is made, the auxiliary classifiers are dropped off. Similar observations are made for FIG. 8. For demonstration, Tables 4 and 5 list the IQA results of EGD and of colonoscopy, respectively, while Table 6 lists comparison results on polyp detection among different CNN models. Tables 4-6 are shown in FIG. 9. Through experimental results as shown in FIGS. 7-8, one can see the student networks with less parameters perform similarly or better than the teachers.

Refer to FIG. 3. In certain embodiments of the decision-support system 110, the computing process 300 further comprises step 320 of compressing an individual selected CNN in the plurality of selected CNNs by KD to reduce a model complexity of the individual selected CNN such that the individual selected CNN as compressed is used to process the sequence of endoscopic images 155 to perform one or more corresponding decision-support tasks associated with the individual selected CNN. As a result, it further reduces the computation-resource requirement of the one or more computers 120.

Figure 10:
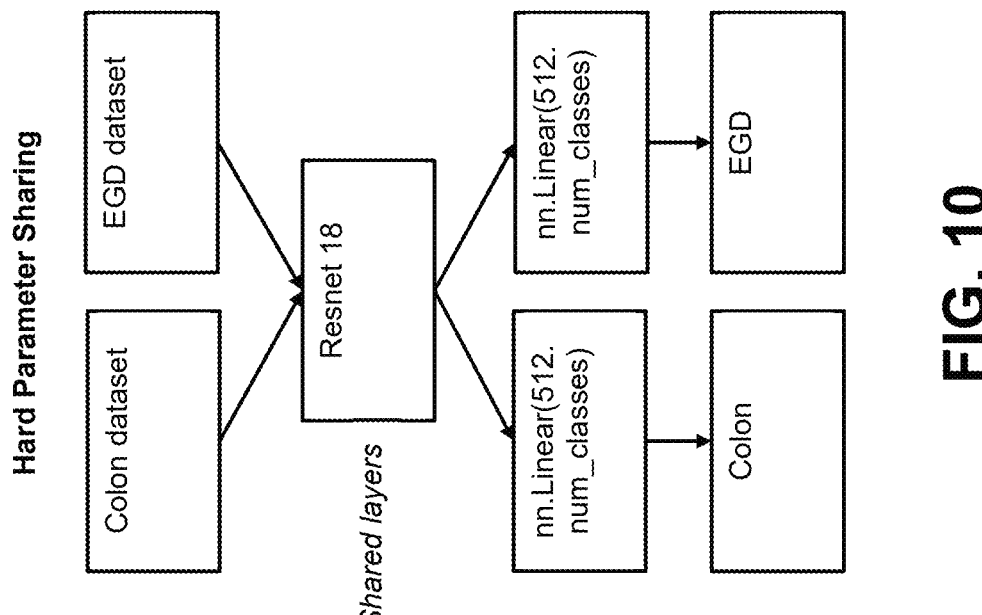
FIG. 10 depicts, for illustration, an example of multi-task CNN that employs HPS.
Figure 11:
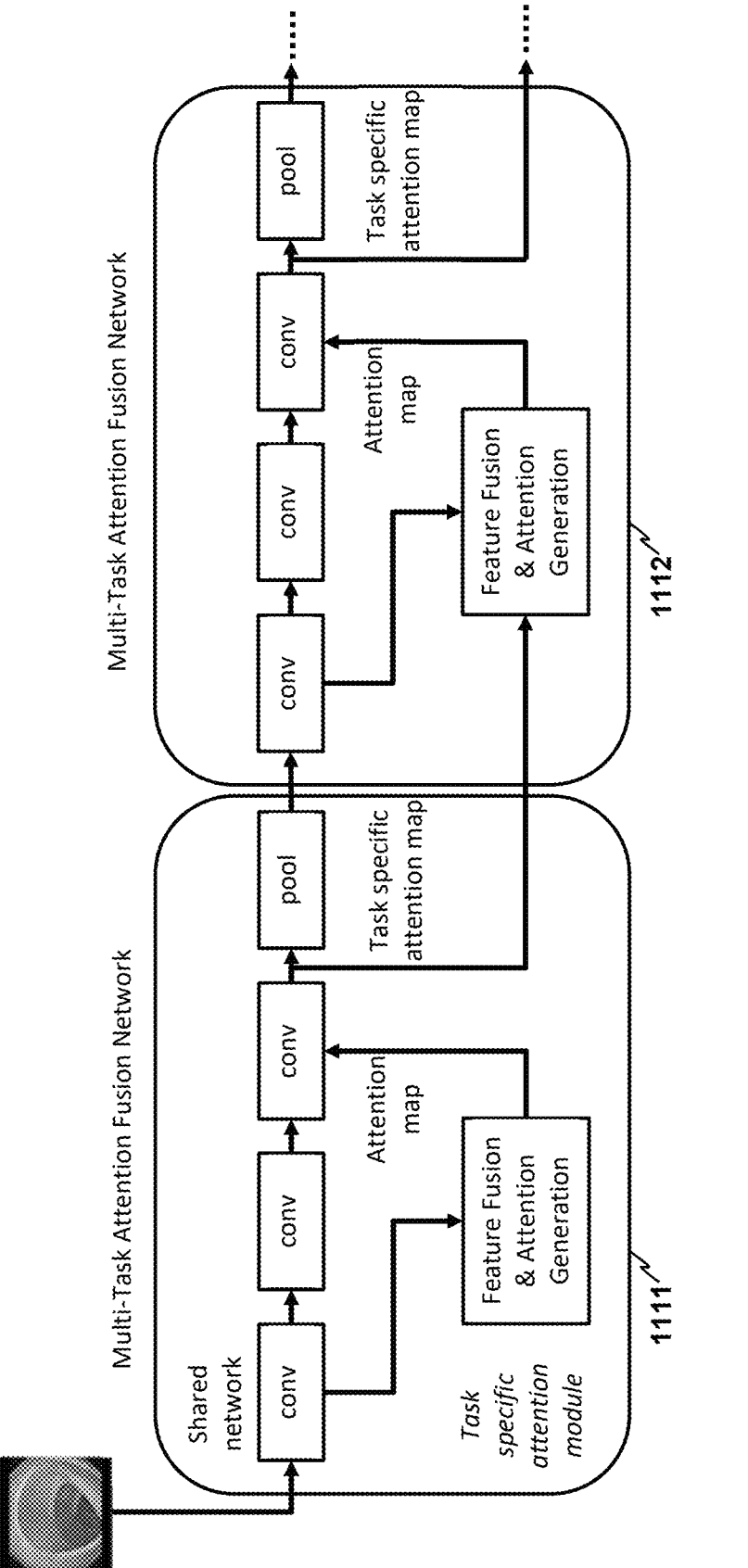
FIG. 11 depicts, for illustration, an example of multi-task CNN that employs MTAFN.

The computation-resource requirement of the one or more computers 120 may be further reduced by utilizing multi-task model sharing. Multi-task model sharing can be applied to the computing process 300 since the computing process 300 involves execution of multiple tasks, and since some model features and results may be re-used to save the computation resources of the one or more computers 120. Two kinds of multi-task model sharing methods may be used, namely, HPS and MTAFN. In HPS, the feature extraction network is shared. The input samples and classifiers are different for different tasks. For illustration, FIG. 10 depicts an example of a multi-task CNN that employs HPS. In MTAFN, additional attention layers that are specific to different tasks are used. FIG. 11 depicts, for illustration, an example of a multi-task CNN that employs MTAFNs 1111, 1112.

Table 7, shown on FIG. 12, lists performance data of a multi-task CNN used for performing the task 221 of cleanliness assessment for EGD and for colonoscopy. The performance data indicate that the use of a multi-task model provides a reduction in model complexity while maintaining comparable accuracy. Furthermore, using the multi-task CNN not only helps conserve computation resources but also enables an easier deployment of the multi-task CNN model on small-scale devices.

In certain embodiments of the decision-support system 110, the plurality of CNNs includes one or more multi-task CNNs. An individual multi-task CNN is used for performing plural corresponding decision-support tasks in the plurality of decision-support tasks 205. Refer to FIG. 3. In one embodiment, at least one multi-task CNN is formed with one or more layers shared by the plural corresponding decision-support tasks in the step 310 of setting up the plurality of CNNs. It thereby further reduces the computation requirement of the one or more computers 120. In another embodiment, at least one multi-task CNN is formed with a serial cascade of MTAFNs in the step 310, thereby further reducing the computation-resource requirement of the one or more computers 120.

Other improvements to the decision-support system 110 are detailed as follows.

It is user-friendly if the decision-support system 110 can be automatically configured for EGD or colonoscopy without a need for the endoscopist to input to the decision-support system 110 the type of GI endoscopic examination that he or she is performing. Automatic configuration for EGD or colonoscopy is achievable by the decision-support system 110 based on an intelligent detection of use scenarios. In particular, the computing process 300 continuously monitors a status of the endoscopic probe of the endoscope 150. The endoscopic probe may be positioned in vitro or in vivo. If the endoscopic probe is positioned in vivo, the decision-support system 110 proceeds to detect if the GI endoscopic examination is EGD or colonoscopy based on detection results from a classification model, which is based on features from the IQA. If the endoscopy type is correctly detected, corresponding CNNs can be loaded into the one or more computers 120 for subsequent operations.

To achieve automatic configuration, the decision-support system 110 is configured as follows. In certain embodiments, the plurality of decision-support tasks 205 is partitioned into a first plurality of tasks performed in EGD, a second plurality of tasks performed in colonoscopy, and a third plurality of tasks performed in both EGD and colonoscopy. In addition, the third plurality of tasks includes the task 214 of determining an imaging location in an upper or lower GI tract so as to determine whether EGD or colonoscopy is carried out. Refer to FIG. 3. The computing process 300 further comprises an additional initialization step 330, and the subprocess 365 further comprises a conditionally updating step 350. In the additional initialization step 330, the plurality of selected tasks is initialized as the third plurality of tasks before an initial execution of the subprocess 365. Herein the initial execution of the subprocess 365 means the first execution of the subprocess 365 in executing the computing process 300. The step 350 is elaborated as follows. If the imaging location is determined to be in the upper GI tract during performing the plurality of selected tasks, the plurality of selected tasks is updated by including the first plurality of tasks and removing the second plurality of tasks. If the imaging location is determined to be in the lower GI tract during performing the plurality of selected tasks, the plurality of selected tasks is updated by including the second plurality of tasks and removing the first plurality of tasks. The updating of the plurality of selected tasks from time to time provides automatic configuration of the decision-support system for EGD and colonoscopy.

It is desirable to enhance an accuracy of lesion detection in processing the sequence of endoscopic images 155.

Figure 13:
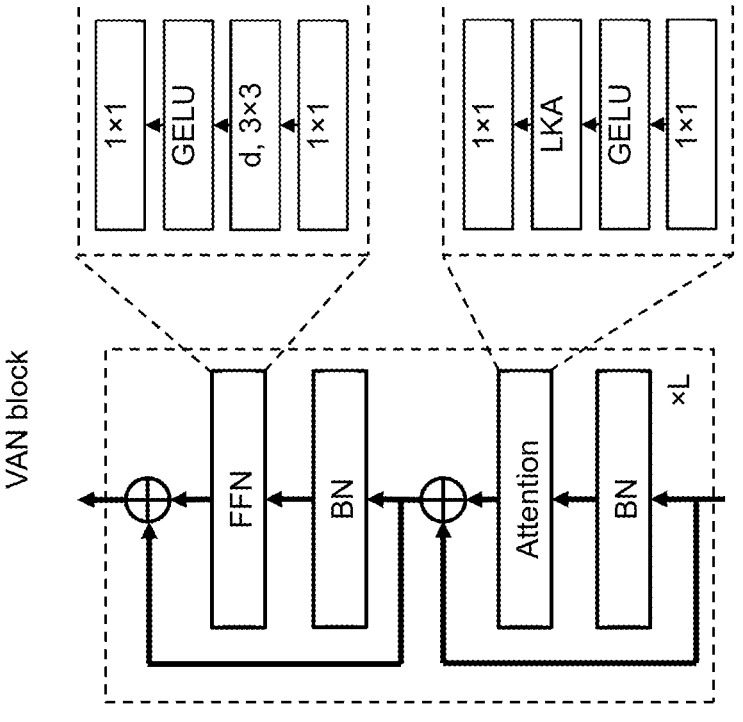
FIG. 13 depicts an example of a VAN usable in the decision-support system for enhancing an accuracy of lesion detection, as well as an example of LKA, on which the VAN is based.

The accuracy of lesion detection in EGD can be enhanced by using a VAN. The VAN is a neural network based on LKA, which enables self-adaptive and long-range correlations in self-attention while avoiding its shortcomings. FIG. 13 depicts examples of the VAN and LKA. The Inventors have obtained this finding based on experiments. In the experiments, lesions on received endoscopic images were categorized into five categories: cancerous lesion; ulcerated lesion; benign polyp; and tumor-like lesion. An evaluation dataset from three hospitals was used in the experiments. The dataset had 4,619 images from 159 individuals, 1,076 of which were malignant, 164 of which were benign lesions, and 3,379 of which were normal. It was found that the VAN model performed much better than the state-of-the-art model (Swin-T). Refer to FIG. 3. In the step 310 of setting up the plurality of CNNs, preferably, a corresponding CNN associated with the task 231 of detecting the lesion in EGD is a VAN.

Attention-guided CNNs and ViTs also help improve the accuracy in colonoscopy, especially based on poor quality datasets. Specifically, the accuracy of lesion detection in colonoscopy can be enhanced by using a ViT utilizing CA. FIG. 14 depicts an example of the CA. Table 8, shown on FIG. 15, lists performance data of lesion detection for two cases, one of which uses a first validation set of poor quality, another one of which uses a second validation set of high quality. The results in Table 8 demonstrate that using the ViT utilizing CA increases robustness in lesion detection against the presence of a validation set of poor quality. Refer to FIG. 3. In the step 310 of setting up the plurality of CNNs, preferably, a corresponding CNN associated with the task 234 of detecting polyp/adenoma in colonoscopy is a ViT utilizing CA.

Figure 16:
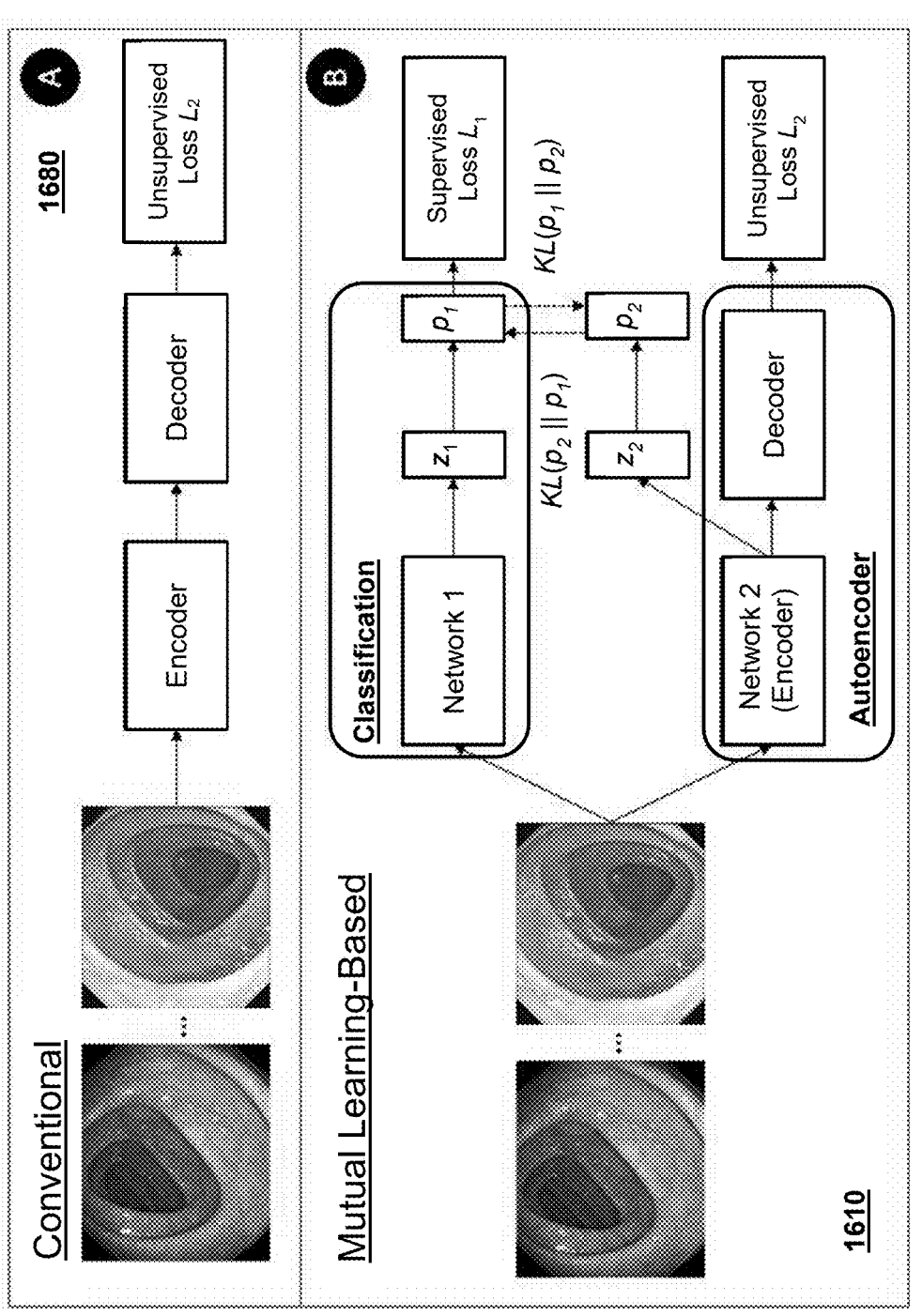
FIG. 16 depicts a conventional CNN arrangement and a CNN arrangement based on mutual learning.

Mutual learning can help improve the performance for identifying a cecum (in the task 223 of classifying an anatomical landmark in colonoscopy) and estimating the withdrawal speed (in the task 224). Mutual learning takes advantage of unsupervised learning to guide supervised learning. FIG. 16 depicts a conventional classifier 1680 and a mutual learning-based classifier 1610. The unsupervised learning in the mutual learning-based classifier 1610 can be trained on a lot of samples without labels, which are quite common in real datasets. Through the guidance from the unsupervised learning model, the model can learn more suitable features from limited samples. It has been found that the mutual learning-based classifier 1610 improves performances of cecum classification and endoscope withdrawal-speed estimation. Controlling the withdrawal speed is of importance since adenoma detection rates increase with longer withdrawal times as mentioned above. Usually, the endoscopist quickly inserts the endoscopic probe to the cecum, and then begins to retrieve the probe relatively slowly to examine if there is any lesion during this retrieval procedure. Hence, the withdrawal speed is monitored during this procedure. If the withdrawal speed is too high, then lesions could be missed. Refer to FIG. 3. In the step 310 of setting up the plurality of CNNs, preferably, a first corresponding CNN associated with the task 223 of classifying the anatomical landmark at the imaging location in colonoscopy is a mutual learning-based model. It is also preferable that in the step 310, a second corresponding CNN associated with the task 224 of estimating the withdrawal speed in colonoscopy is a mutual learning-based model.

It is advantageous to integrate lesion-detection results of the plurality of lesion-detection tasks 230 with quality-control results generated from the plurality of quality-control tasks 220. By this integration, value-added results, which are more valuable to the endoscopist than separately considering the lesion-detection results and quality-control results, are generated. However, a main issue of integrating lesion detection and quality control is that there are different latency requirements between lesion detection and quality control. Lesion detection requires low latency in processing image frames with minimum dropped frames while efficient inference of quality control allows acceptable latency. Due to the different latency requirements, there is a need for multiprocessing-based inference, one process for making inference for lesion detection and another one for quality control. To fulfil system design requirements including addressing the different latency requirements, one needs to ensure no accuracy drop caused by the dropped frames, and to output analytic results in real-time.

Figure 17:
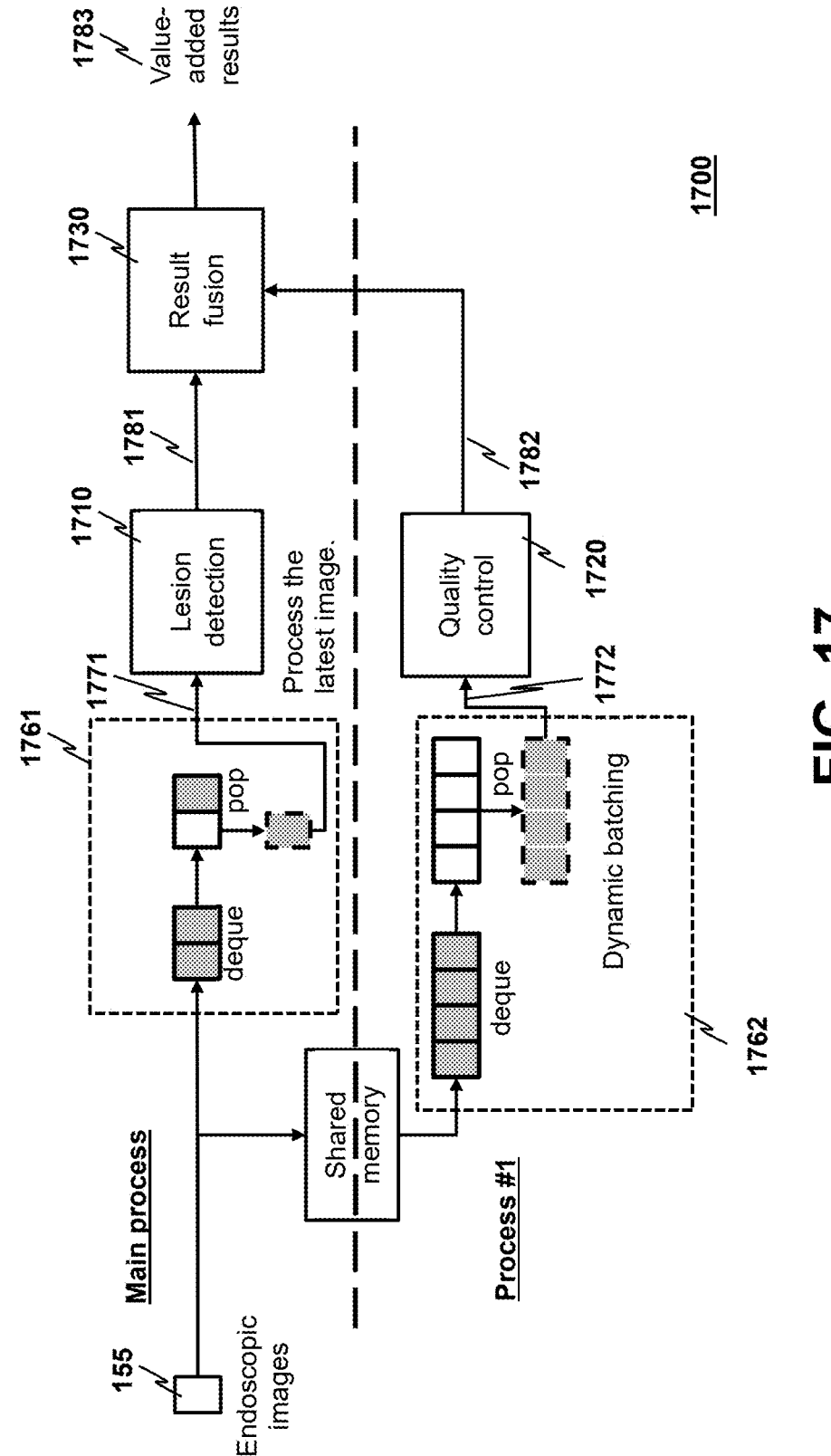
FIG. 17 depicts a workflow for seamlessly integrating lesion detection and quality control while fulfilling system design requirements and addressing different latency requirements.

FIG. 17 depicts a workflow 1700 for seamlessly integrating lesion detection and quality control while fulfilling the system design requirements. It is preferable and advantageous to include executing the workflow 1700 in the step 340 of performing the plurality of selected tasks and the step 345 of post-processing results generated from performing the plurality of selected tasks. Consider that the plurality of selected tasks includes one or more selected lesion-detection tasks and one or more selected quality-control tasks. The one or more selected lesion-detection tasks are selected from the plurality of lesion-detection tasks 230. The one or more selected quality-control tasks are selected from the plurality of quality-control tasks 220.

In the workflow 1700, the sequence of endoscopic images 155 is buffered with a first buffering scheme 1761 to yield a first buffered sequence of endoscopic images 1771. The first buffered sequence 1771 is used in a step 1710 of performing the one or more selected lesion-detection tasks to generate lesion-detection results 1781. In particular, the first buffering scheme 1761 is arranged to generate the first buffered sequence 1771 with a first latency that satisfies a first set of latency requirements required by the one or more selected lesion-detection tasks in receiving the sequence of endoscopic images 155. In the step 1710, the first buffered sequence 1771 is used as an input to the one or more selected lesion-detection tasks, and the one or more selected lesion-detection tasks generate the lesion-detection results 1781.

Similarly, the sequence of endoscopic images 155 is also buffered with a second buffering scheme 1762 to yield a second buffered sequence of endoscopic images 1772. The second buffered sequence 1772 is used in a step 1720 of performing the one or more selected quality-control tasks to generate quality-control results 1782. The second buffering scheme 1762 is arranged to generate the second buffered sequence 1772 with a second latency that satisfies a second set of latency requirements required by the one or more selected quality-control tasks in receiving the sequence of endoscopic images 155. In the step 1720, the second buffered sequence 1772 is used as an input to the one or more selected quality-control tasks, and the one or more selected quality-control tasks generate the quality-control results 1782.

Note that the first set of latency requirements is set according to appropriate low-latency requirements demanded by the one or more selected lesion-detection tasks, while the second set of latency requirements is set according to more-relaxed latency requirements of the one or more selected quality-control tasks. It follows that the first latency is lower, usually considerably lower, than the second latency. Preferably, the first buffering scheme 1761 uses a dropping mechanism in generating the first buffered sequence 1771 to achieve the first latency. The dropping mechanism is simple to implement. It is also preferable that the second buffering scheme 1762 uses dynamic batching inference in generating the second buffered sequence 1772 to increase efficiency of GPU use while achieving the second latency. The increased efficiency of GPU use means an increased utilization of GPUs in the one or more computers 120 provided that the GPUs are installed in the one or more computers 120.

The lesion-detection results 1781 and the quality-control results 1782 are integrated or fused together in a result-fusion step 1730 to generate one or more value-added results 1783.

Note that when the workflow 1700 is incorporated in the computing process 300, the steps 1710 and 1720 are included in the step 340 while the step 1730 is included in the step 345.

Implementation models of organizing different decision-support tasks in the computing process 300 for EGD and colonoscopy with result fusion are illustrated by examples as follows.

Figure 18:
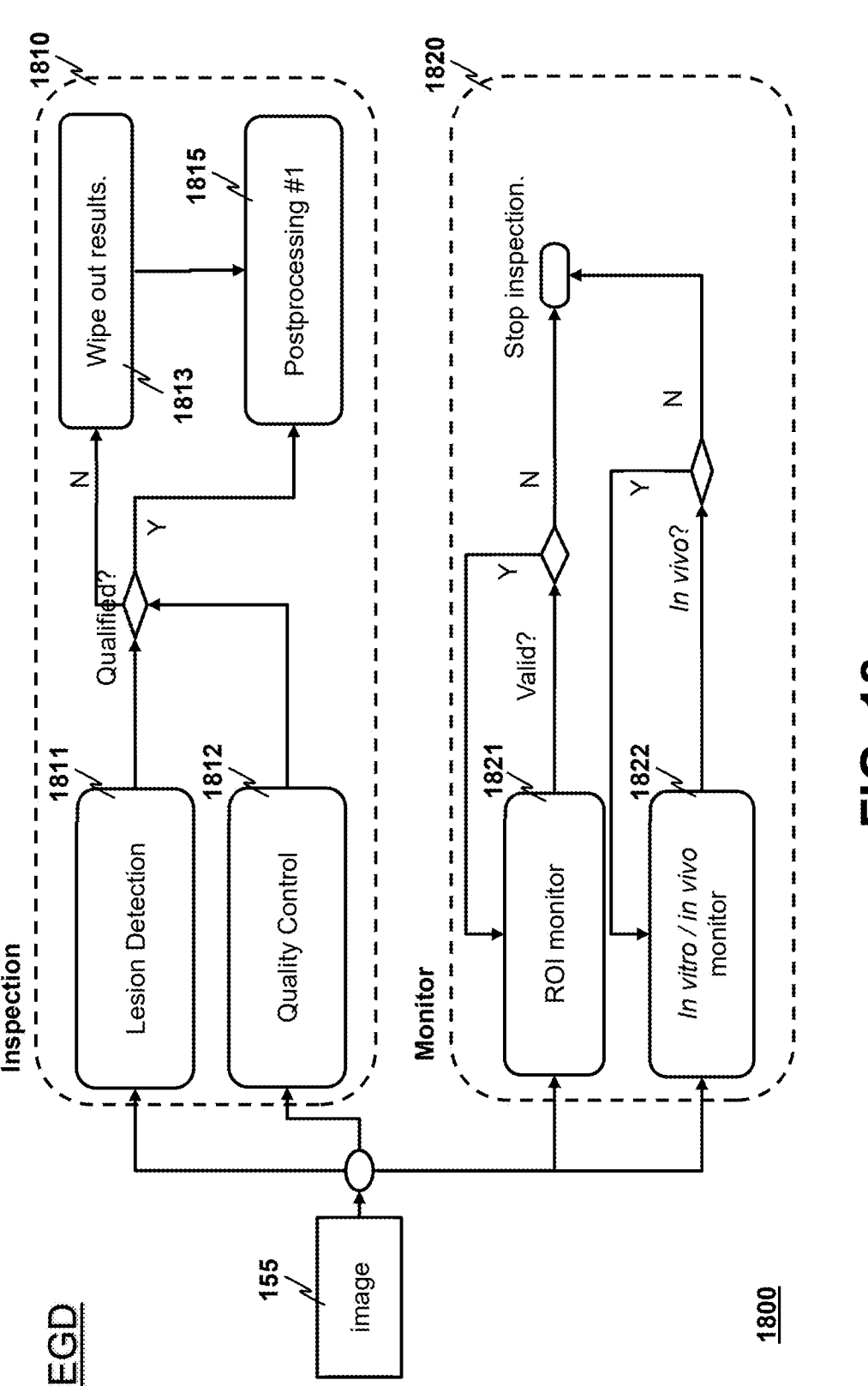
FIG. 18 depicts a first simplified implementation model of the computing process for providing decision-support functions in EGD.
Figure 18:
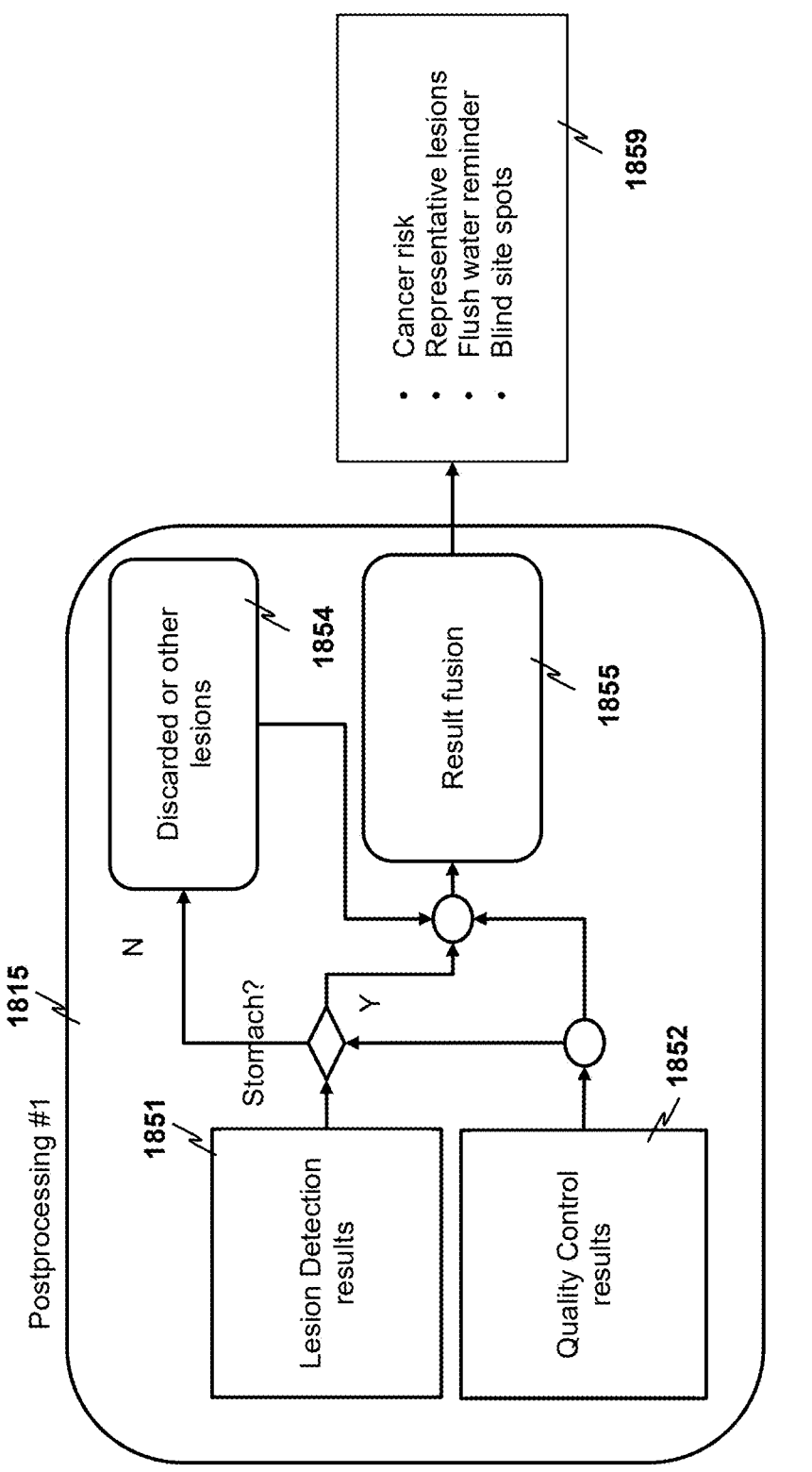

FIG. 18 depicts a first simplified implementation model 1800 of the computing process 300 for providing decision-support functions in EGD. The model 1800 comprises an inspection module 1810 for inspecting the human subject, and a monitoring module 1820 for real-time monitoring if the imaging location is in an upper GI tract.

The monitoring module 1820 includes a ROI monitor 1821 for performing the task 212 of detecting a ROI on an image captured at the imaging location where the ROI is a region in the upper GI tract, and an in vitrol in vivo monitor 1822 for performing the task 211 of classifying the imaging location as an in vivo location or an in vitro one. The ROI monitor 1821 performs the task 212 from time to time because during the GI endoscopic examination, the ROI could be changed. The monitoring module 1820 stops the inspection module 1810 from doing lesion detection and quality control if the monitoring module 1820 finds that the imaging location is outside the human subject or is not in the upper GI tract.

In the inspection module 1810, lesion detection 1811 and quality control 1812 are performed. If a quality-control result indicates that a corresponding lesion-detection result is unreliable, the corresponding lesion-detection result is not qualified and is wiped out (1813). Generally, the wipe-out operation 1813 reduces false positives of detected lesions. A first postprocessing block 1815 in the inspection module 1810 receives qualified lesion-detection and quality-control results.

The first postprocessing block 1815 first determines if lesion-detection results 1851 are obtained for the stomach according to quality-control results 1852. Corresponding lesion-detection results obtained outside the stomach are either discarded or classified as other lesions (1854). Nondiscarded lesion-detection results are integrated with the quality-control results 1852 in a result-fusion block 1855. Particularly, relationships between identified stomach sites and lesions are used to further improve the lesion-detection performance. The result-fusion block 1855 generates a set of value-added results 1859. Examples of value-added results 1859 include an estimated degree of cancer risk, a set of one or more identified representative lesions, a reminder of flushing water for improving quality of subsequently captured images, and a set of one or more blind site spots identified missing in the sequence of endoscopic images 155.

Figure 19:
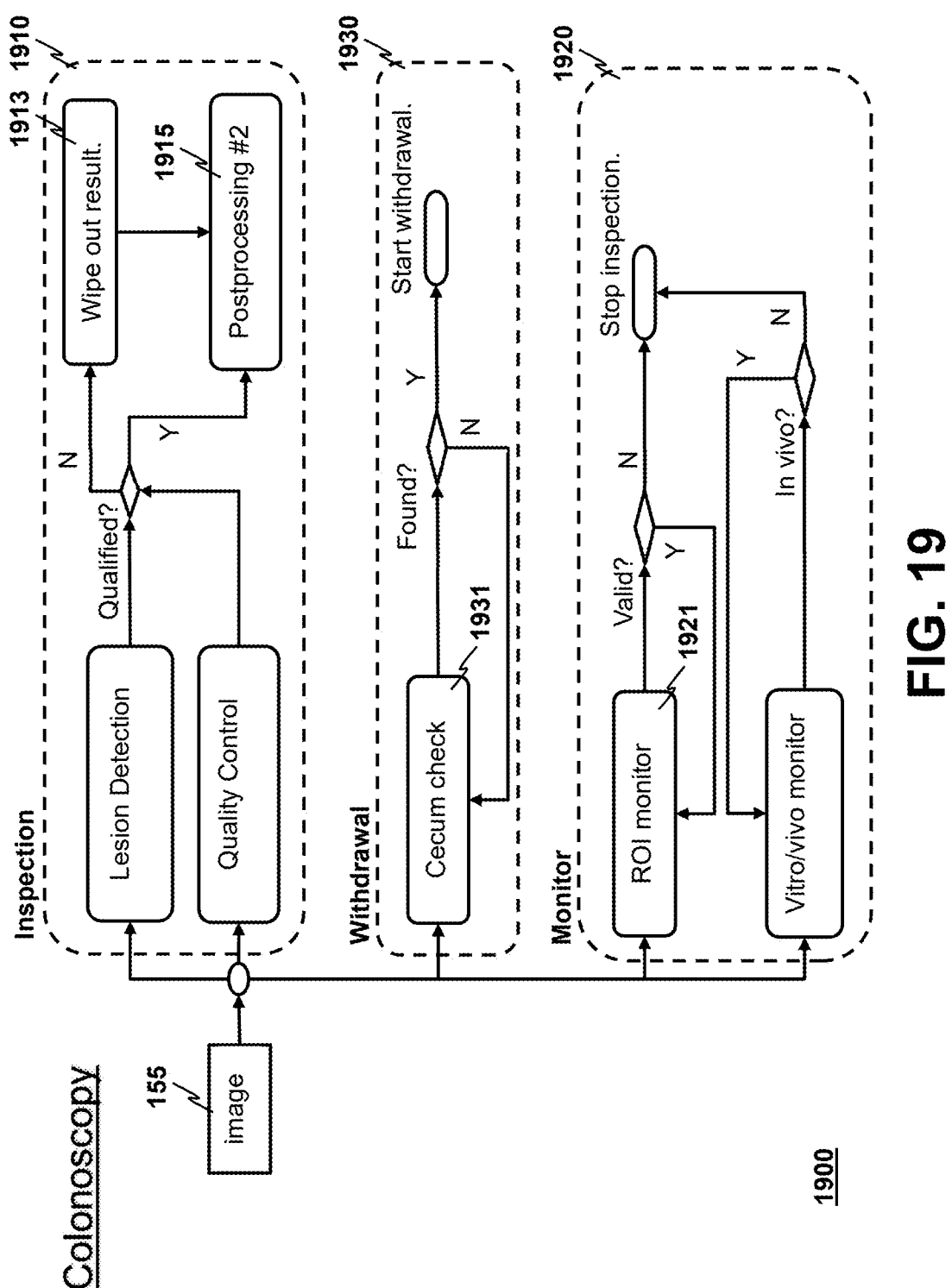
FIG. 19 depicts a second simplified implementation model of the computing process for providing decision-support functions in colonoscopy.
Figure 19:
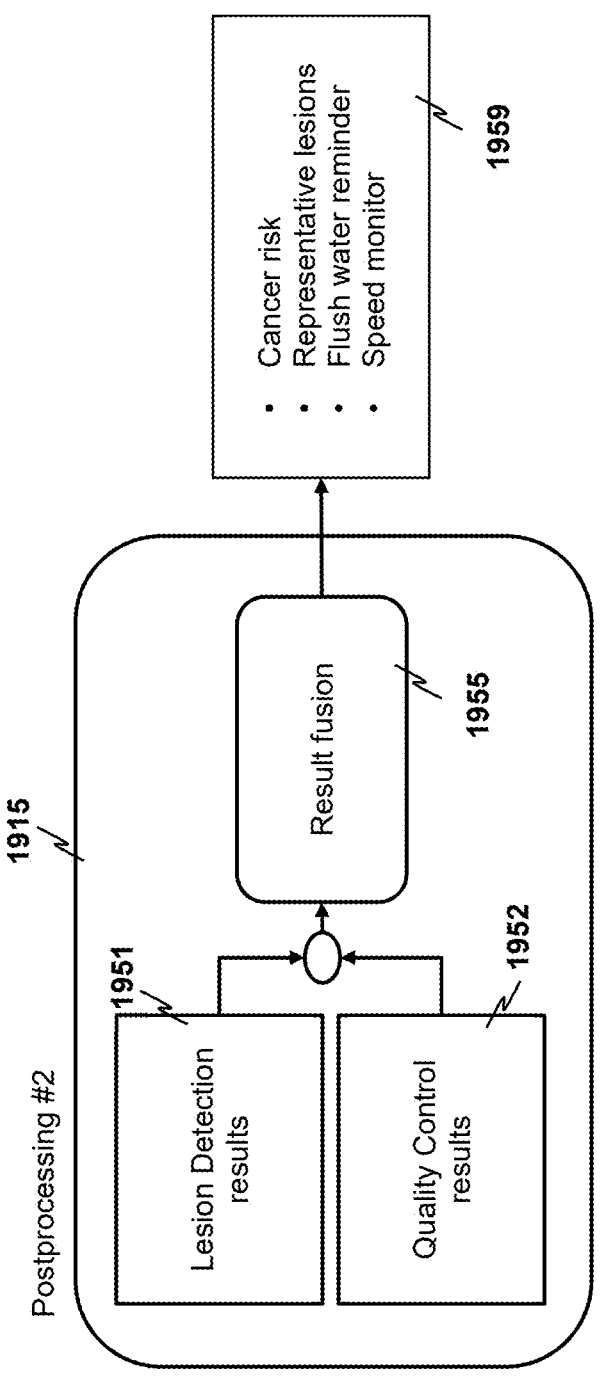

FIG. 19 depicts a second simplified implementation model 1900 of the computing process 300 for providing decision-support functions in colonoscopy. The model 1900 comprises an inspection module 1910 for inspecting the human subject, a withdrawal module 1930 for detecting arrival at the human subject's cecum so as to indicate withdrawal of the endoscopic probe from inside the human subject for starting inspection of the human subject's colon, and a monitoring module 1920 for real-time monitoring if the imaging location is in a lower GI tract.

The withdrawal module 1930 includes a cecum checker 1931 for performing the task 223 of classifying an anatomical landmark at the imaging location as cecum. The cecum checker 1931 indicates a starting point for the endoscopist to withdraw the endoscopic probe from the human subject as well as for initiating the inspection module 1910 to do lesion detection and quality control.

The monitoring module 1920 for colonoscopy is similar to the monitoring module 1820 for EGD except that a ROI monitor 1921 in the monitoring module 1920 is configured with the ROI being a region in the lower GI tract. Those skilled in the art will be able to understand structural and functional details of the monitoring module 1920 for colonoscopy with reference to the monitoring module 1820 for EGD as disclosed herein.

The inspection module 1910 for colonoscopy is similar in structure and function to the inspection module 1810 for EGD. Those skilled in the art will be able to understand structural and functional details of the inspection module 1910 for colonoscopy with reference to the inspection module 1810 for EGD as disclosed herein. Similarly, a wipe-out operation 1913 in the inspection module 1910 reduces false positives of detected lesions. A second postprocessing block 1915 in the inspection module 1910 receives qualified lesion-detection and quality-control results.

In the second postprocessing block 1915, the lesion-detection results 1951 and quality-control results 1952 as received are integrated in a result-fusion block 1955 to yield a set of value-added results 1959. Examples of value-added results 1959 include an estimated degree of cancer risk, a set of one or more identified representative lesions, a reminder of flushing water for improving quality of subsequently captured images, and an estimated withdrawal speed as a feedback to the endoscopist for setting a desired speed of withdrawal.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A decision-support system for gastrointestinal (GI) endoscopy, the system comprising one or more computers configured to execute a computing process for processing a sequence of endoscopic images acquired in a GI endoscopic examination to at least perform a plurality of selected tasks dynamically selected from a plurality of decision-support tasks, the computing process comprising:

setting up a plurality of convolutional neural networks (CNNs) for performing the plurality of decision-support tasks according to the sequence of endoscopic images, an individual CNN being modeled with one or more learnable kernels, wherein each learnable kernel used in the plurality of CNNs is modeled as a linear combination of a set of fixed kernels with the set of fixed kernels being invariant over the plurality of CNNs so as to simplify kernel learning in comparison to training a conventional CNN model with unrestricted one or more kernels to thereby reduce a computation-resource requirement of the one or more computers and hence enable the decision-support system to be realized as an edge computing system near a site of performing the GI endoscopic examination;

executing a subprocess, wherein the subprocess comprises performing the plurality of selected tasks by processing the sequence of endoscopic images with each CNN in a plurality of selected CNNs, the plurality of selected CNNs being identified from the plurality of CNNs and being used for performing the plurality of selected tasks; and repeating the subprocess until an event indicative of exiting from looping the subprocess occurs.

2. The decision-support system of claim 1, wherein each kernel in the set of fixed kernels is a 3×3 matrix.

3. The decision-support system of claim 1, wherein the computing process further comprises compressing an individual selected CNN in the plurality of selected CNNs by knowledge distillation to reduce a model complexity of the individual selected CNN such that the individual selected CNN as compressed is used to process the sequence of endoscopic images to perform one or more corresponding decision-support tasks associated with the individual selected CNN to thereby further reduce the computation-resource requirement of the one or more computers.

4. The decision-support system of claim 1, wherein:

the plurality of CNNs includes one or more multi-task CNNs, an individual multi-task CNN being used for performing plural corresponding decision-support tasks in the plurality of decision-support tasks; and in the setting up of the plurality of CNNs, at least one multi-task CNN is formed with one or more layers shared by the plural corresponding decision-support tasks to thereby further reduce the computation-resource requirement of the one or more computers.

5. The decision-support system of claim 1, wherein:

the plurality of CNNs includes one or more multi-task CNNs, an individual multi-task CNN being used for performing plural corresponding decision-support tasks in the plurality of decision-support tasks; and in the setting up of the plurality of CNNs, at least one multi-task CNN is formed with a serial cascade of multi-task attention fusion networks to thereby further reduce the computation-resource requirement of the one or more computers.

6. The decision-support system of claim 1, wherein:

the plurality of decision-support tasks is partitioned into a first plurality of tasks performed in esophagogastroduodenoscopy (EGD), a second plurality of tasks performed in colonoscopy, and a third plurality of tasks performed in both EGD and colonoscopy;

the third plurality of tasks includes the task of determining an imaging location in an upper or lower GI tract so as to determine whether EGD or colonoscopy is carried out;

the computing process further comprises initializing the plurality of selected tasks as the third plurality of tasks before an initial execution of the subprocess; and the subprocess further comprises:

if the imaging location is determined to be in the upper GI tract during performing the plurality of selected tasks, then updating the plurality of selected tasks by including the first plurality of tasks and removing the second plurality of tasks; and if the imaging location is determined to be in the lower GI tract during performing the plurality of selected tasks, then updating the plurality of selected tasks by including the second plurality of tasks and removing the first plurality of tasks, whereby the updating of the plurality of selected tasks from time to time provides automatic configuration of the decision-support system for EGD and colonoscopy.

7. The decision-support system of claim 1, wherein:

the plurality of decision-support tasks includes a plurality of preparation tasks, a plurality of quality-control tasks and a plurality of lesion-detection tasks;

the plurality of preparation tasks includes tasks of: classifying an imaging location as an in vivo location or an in vitro one; detecting a region of interest (ROI) on an image captured at the imaging location; assessing an image quality achieved at the imaging location; and determining the imaging location in an upper or lower GI tract so as to determine whether esophagogastroduo-denoscopy (EGD) or colonoscopy is carried out;

the plurality of quality-control tasks includes tasks of: assessing a level of cleanliness at the imaging location; classifying a stomach site in EGD; classifying an anatomical landmark at the imaging location in colonoscopy; and estimating a withdrawal speed in colonoscopy; and the plurality of lesion-detection tasks includes tasks of: detecting a lesion in EGD; identifying a cancer in EGD; detecting *Helicobacter pylori* (HP) infection in EGD; detecting polyp/adenoma in colonoscopy; and identifying a cancer in colonoscopy.

8. The decision-support system of claim 7, wherein the anatomical landmark is classified as a terminal ileum, a cecum, an ascending colon, a traverse colon, a descending colon, a sigmoid colon, a rectum, or an anus.

9. The decision-support system of claim 7, wherein the computing process further comprises performing one or more reporting tasks selected from tasks of: reporting the assessed level of cleanliness; reporting a HP degree in EGD; reporting a level of cancer risk; reporting key images of lesion/polyp as extracted from the sequence of endoscopic images; and reporting key images of stomach sites/anatomical landmarks as extracted from the sequence of endoscopic images.

10. The decision-support system of claim 1, wherein:

the plurality of decision-support tasks includes a plurality of lesion-detection tasks;

the plurality of lesion-detection tasks includes a task of detecting a lesion in EGD; and in the setting up of the plurality of CNNs, a corresponding CNN associated with the task of detecting the lesion in EGD is a visual attention network (VAN).

11. The decision-support system of claim 1, wherein:
the plurality of decision-support tasks includes a plurality of lesion-detection tasks;
the plurality of lesion-detection tasks includes a task of detecting polyp/adenoma in colonoscopy; and
in the setting up of the plurality of CNNs, a corresponding CNN associated with the task of detecting polyp/adenoma in colonoscopy is a visual transformer (ViT) utilizing coordinate attention (CA).

12. The decision-support system of claim 1, wherein:
the plurality of decision-support tasks includes a plurality of quality-control tasks;
the plurality of quality-control tasks includes a task of classifying an anatomical landmark at an imaging location in colonoscopy; and
in the setting up of the plurality of CNNs, a corresponding CNN associated with the task of classifying the anatomical landmark at the imaging location in colonoscopy is a mutual learning-based model.

13. The decision-support system of claim 1, wherein:
the plurality of decision-support tasks includes a plurality of quality-control tasks;
the plurality of quality-control tasks includes a task of estimating a withdrawal speed in colonoscopy; and
in the setting up of the plurality of CNNs, a corresponding CNN associated with the task of estimating the withdrawal speed in colonoscopy is a mutual learning-based model.

14. The decision-support system of claim 1, wherein:
the plurality of decision-support tasks includes a plurality of quality-control tasks and a plurality of lesion-detection tasks;
the plurality of selected tasks includes one or more selected lesion-detection tasks and one or more selected quality-control tasks, the one or more selected lesion-detection tasks being selected from the plurality of lesion-detection tasks, the one or more selected quality-control tasks being selected from the plurality of quality-control tasks;
the performing of the plurality of selected tasks comprises:
buffering the sequence of endoscopic images with a first buffering scheme to yield a first buffered sequence of endoscopic images, the first buffered sequence being used for performing the one or more selected lesion-detection tasks, wherein the first buffering scheme is arranged to generate the first buffered sequence with a first latency that satisfies a first set of latency requirements required by the one or more selected lesion-detection tasks in receiving the sequence of endoscopic images;
performing the one or more selected lesion-detection tasks to generate lesion-detection results, an input to the one or more selected lesion-detection tasks being the first buffered sequence;
buffering the sequence of endoscopic images with a second buffering scheme to yield a second buffered sequence of endoscopic images, the second buffered sequence being used for performing the one or more selected quality-control tasks, wherein the second buffering scheme is arranged to generate the second buffered sequence with a second latency that satisfies a second set of latency requirements required by the one or more selected quality-control tasks in receiving the sequence of endoscopic images; and
performing the one or more selected quality-control tasks to generate quality-control results, an input to the one or more selected quality-control tasks being the second buffered sequence; and
the subprocess further comprises post-processing results generated from performing the plurality of selected tasks, wherein the post-processing of the generated results comprises integrating the lesion-detection results and quality-control results to generate one or more value-added results.

15. The decision-support system of claim 14, wherein:
the one or more computers include one or more graphics processing units (GPUs);
the first latency is lower than the second latency;
the first buffering scheme uses a dropping mechanism in generating the first buffered sequence to achieve the first latency; and
the second buffering scheme uses dynamic batching inference in generating the second buffered sequence to increase an efficiency of GPU use in the one or more computers while achieving the second latency.

16. The decision-support system of claim 14, wherein the one or more value-added results are selected from a group consisting of an estimated degree of cancer risk, a set of one or more identified representative lesions, a reminder of flushing water for improving quality of subsequently captured images, an estimated withdrawal speed in colonoscopy, and a set of one or more blind site spots identified missing in the sequence of endoscopic images in EGD.

17. The decision-support system of claim 1, wherein the one or more computers are configured to receive a sequence of video frames as the sequence of endoscopic images.

18. The decision-support system of claim 1, wherein each of the one or more computers is portable, and the decision-support system is configured to be portable.

19. The decision-support system of claim 1, wherein:
the computing process further comprises performing one or more reporting tasks for reporting results obtained from performing the plurality of selected tasks; and
the decision-support system further comprises a display for visually displaying the obtained results.

20. A gastrointestinal (GI) endoscopic system for conducting a GI endoscopic examination on a human subject, the GI endoscopic examination being of a type selected from esophagogastroduodenoscopy (EGD) and colonoscopy, the system comprising:
an endoscope for inspecting the human subject in the GI endoscopic examination to thereby yield a sequence of endoscopic images, the endoscope being configured to perform the GI endoscopic examination of the selected type; and
the decision-support system of claim 1 for processing the sequence of endoscopic images.

* * * * *